(12) United States Patent
Simpson et al.

(10) Patent No.: US 12,151,049 B2
(45) Date of Patent: Nov. 26, 2024

(54) METHODS FOR MANUFACTURING RADIOPAQUE INTRALUMINAL STENTS COMPRISING COBALT-BASED ALLOYS WITH SUPERSATURATED TUNGSTEN CONTENT

(71) Applicant: Abbott Cardiovascular Systems, Inc., Santa Clara, CA (US)

(72) Inventors: John A. Simpson, Carlsbad, CA (US); Puneet Kamal Singh Gill, Anaheim, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 193 days.

(21) Appl. No.: 17/068,526

(22) Filed: Oct. 12, 2020

(65) Prior Publication Data
US 2021/0106729 A1  Apr. 15, 2021

Related U.S. Application Data

(60) Provisional application No. 62/914,806, filed on Oct. 14, 2019.

(51) Int. Cl.
*A61L 31/02* (2006.01)
*A61L 31/18* (2006.01)
*B22F 3/16* (2006.01)
*B22F 9/08* (2006.01)
(Continued)

(52) U.S. Cl.
CPC .............. *A61L 31/022* (2013.01); *A61L 31/18* (2013.01); *B22F 3/16* (2013.01); *B22F 9/08* (2013.01); *C22C 1/02* (2013.01); *C22C 30/00* (2013.01)

(58) Field of Classification Search
None
See application file for complete search history.

(56) References Cited

U.S. PATENT DOCUMENTS

| | | | |
|---|---|---|---|
| 2,938,850 A | 5/1960 | Hans | |
| 3,203,884 A | 8/1965 | Heinz et al. | |
| 3,612,058 A | 10/1971 | Ackerman | |

(Continued)

FOREIGN PATENT DOCUMENTS

| | | | |
|---|---|---|---|
| CN | 101115869 A | | 1/2008 |
| CN | 101554685 A | * | 10/2009 |

(Continued)

OTHER PUBLICATIONS

Tanaka. Effects of high-temperature ageing on the creep-rupture properties of high-tungsten cobalt-base superalloys. Journal of Materials Science 29 (1994) 2620-2628. (Year: 1994).*

(Continued)

*Primary Examiner* — Paul A Wartalowicz
*Assistant Examiner* — Stephani Hill
(74) *Attorney, Agent, or Firm* — Workman Nydegger; Randy Shen

(57) ABSTRACT

Embodiments are directed to radiopaque implantable structures (e.g., stents) formed of cobalt-based alloys that comprise cobalt, chromium, tungsten, and nickel, and methods for their manufacture. Tungsten is present above its solubility limit (about 15%) at ambient temperature, but is still only present as a super-saturated, primarily single-phase material exhibiting an FCC microcrystalline structure.

21 Claims, 11 Drawing Sheets

(51) Int. Cl.
   *C22C 1/02* (2006.01)
   *C22C 30/00* (2006.01)

(56) References Cited

U.S. PATENT DOCUMENTS

| | | | |
|---|---|---|---|
| 3,635,703 A | 1/1972 | Pissarevsky |
| 3,937,628 A | 2/1976 | Watanabe et al. |
| 4,127,459 A | 11/1978 | Jumer |
| 4,330,381 A | 5/1982 | Jumer |
| 4,654,092 A | 3/1987 | Melton |
| 4,685,977 A | 8/1987 | Chang |
| 4,846,186 A | 7/1989 | Box et al. |
| 4,854,330 A | 8/1989 | Evans et al. |
| 4,967,753 A | 11/1990 | Haase et al. |
| 5,061,275 A | 10/1991 | Wallsten et al. |
| 5,067,489 A | 11/1991 | Lind |
| 5,069,226 A | 12/1991 | Yamauchi et al. |
| 5,147,317 A | 9/1992 | Shank et al. |
| 5,171,383 A | 12/1992 | Sagae et al. |
| 5,174,295 A | 12/1992 | Christian et al. |
| 5,174,302 A | 12/1992 | Palmer |
| 5,184,621 A | 2/1993 | Vogel et al. |
| 5,238,004 A | 8/1993 | Sahatjian et al. |
| 5,287,858 A | 2/1994 | Hammerslag et al. |
| 5,330,826 A | 7/1994 | Taylor et al. |
| 5,353,798 A | 10/1994 | Sieben |
| 5,353,808 A | 10/1994 | Viera |
| 5,354,623 A | 10/1994 | Hall |
| 5,404,887 A | 4/1995 | Prather |
| 5,421,955 A | 6/1995 | Lau et al. |
| 5,433,200 A | 7/1995 | Fleischhacker, Jr. |
| 5,449,369 A | 9/1995 | Imran |
| 5,480,382 A | 1/1996 | Hammerslag et al. |
| 5,514,154 A | 5/1996 | Lau et al. |
| 5,569,295 A | 10/1996 | Lam |
| 5,603,721 A | 2/1997 | Lau et al. |
| 5,618,299 A | 4/1997 | Khosravi et al. |
| 5,628,787 A | 5/1997 | Mayer |
| 5,630,840 A | 5/1997 | Mayer |
| 5,636,641 A | 6/1997 | Fariabi |
| 5,649,952 A | 7/1997 | Lam |
| 5,666,969 A | 9/1997 | Urick et al. |
| 5,673,707 A | 10/1997 | Chandrasekaran |
| 5,695,111 A | 12/1997 | Nanis |
| 5,716,400 A | 2/1998 | Davidson |
| 5,716,417 A | 2/1998 | Girard et al. |
| 5,725,572 A | 3/1998 | Lam et al. |
| 5,728,158 A | 3/1998 | Lau et al. |
| 5,735,893 A | 4/1998 | Lau et al. |
| 5,746,701 A | 5/1998 | Noone |
| 5,759,192 A | 6/1998 | Saunders |
| 5,766,238 A | 6/1998 | Lau et al. |
| 5,776,080 A | 7/1998 | Thome et al. |
| 5,788,654 A | 8/1998 | Schwager |
| 5,797,857 A | 8/1998 | Obitsu |
| 5,799,386 A | 9/1998 | Ingersoll et al. |
| 5,803,344 A | 9/1998 | Stankavich et al. |
| 5,824,077 A | 10/1998 | Mayer |
| 5,849,037 A | 12/1998 | Frid |
| 5,858,556 A | 1/1999 | Eckert et al. |
| 5,865,767 A | 2/1999 | Frechette et al. |
| 5,876,432 A | 3/1999 | Lau et al. |
| 5,891,055 A | 4/1999 | Sauter |
| 5,891,191 A | 4/1999 | Stinson |
| 5,916,178 A | 6/1999 | Noone et al. |
| 5,984,973 A | 11/1999 | Girard et al. |
| 5,985,126 A | 11/1999 | Bleck et al. |
| 6,004,279 A | 12/1999 | Crowley et al. |
| 6,027,528 A | 2/2000 | Tomonto et al. |
| 6,139,511 A | 10/2000 | Huter et al. |
| 6,183,353 B1 | 2/2001 | Frantzen |
| 6,214,200 B1 | 4/2001 | Altena et al. |
| 6,221,096 B1 | 4/2001 | Aiba et al. |
| 6,234,981 B1 | 5/2001 | Howland |
| 6,287,331 B1 | 9/2001 | Heath |
| 6,355,058 B1 | 3/2002 | Pacetti et al. |
| 6,375,826 B1 | 4/2002 | Wang et al. |
| 6,390,992 B1 | 5/2002 | Morris et al. |
| 6,419,693 B1 | 7/2002 | Fariabi |
| 6,500,130 B2 | 12/2002 | Kinsella et al. |
| 6,503,290 B1 * | 1/2003 | Jarosinski ............... C23C 30/00 427/455 |
| 6,508,803 B1 | 1/2003 | Horikawa et al. |
| 6,592,570 B2 | 7/2003 | Abrams et al. |
| 6,599,415 B1 | 7/2003 | Ku et al. |
| 6,602,228 B2 | 8/2003 | Nanis et al. |
| 6,602,272 B2 | 8/2003 | Boylan et al. |
| 6,610,046 B1 | 8/2003 | Usami et al. |
| 6,620,192 B1 | 9/2003 | Jalisi |
| 6,679,980 B1 | 1/2004 | Andreacchi |
| 7,105,018 B1 | 9/2006 | Yip et al. |
| 7,156,869 B1 | 1/2007 | Pacetti |
| 7,208,070 B2 | 4/2007 | Swain |
| 7,244,319 B2 | 7/2007 | Abrams et al. |
| 7,250,058 B1 | 7/2007 | Pacetti et al. |
| 7,252,746 B2 | 8/2007 | Schaeffer |
| 7,294,214 B2 | 11/2007 | Craig |
| 7,318,837 B2 | 1/2008 | Krivoruchko et al. |
| 7,357,854 B1 | 4/2008 | Andreacchi |
| 7,413,574 B2 | 8/2008 | Yip et al. |
| 7,488,343 B2 | 2/2009 | O'Brien et al. |
| 7,494,474 B2 | 2/2009 | Richardson et al. |
| 7,498,062 B2 | 3/2009 | Calcaterra et al. |
| 7,501,048 B2 | 3/2009 | Loermans et al. |
| 7,540,997 B2 | 6/2009 | Stinson |
| 7,601,230 B2 | 10/2009 | Craig |
| 7,632,303 B1 | 12/2009 | Stalker et al. |
| 7,740,798 B2 | 6/2010 | Stinson |
| 7,771,581 B2 | 8/2010 | Callol et al. |
| 7,785,274 B2 | 8/2010 | Mishima et al. |
| 7,883,474 B1 | 2/2011 | Mirigian et al. |
| 8,100,837 B1 | 1/2012 | Cornish et al. |
| 8,267,872 B2 | 9/2012 | Ressemann et al. |
| 8,323,459 B2 | 12/2012 | Andreacchi et al. |
| 8,348,860 B2 | 1/2013 | Murayama et al. |
| 8,360,995 B2 | 1/2013 | Elsesser et al. |
| 8,430,923 B2 | 4/2013 | Pacetti et al. |
| 8,529,710 B2 | 9/2013 | Ishida et al. |
| 8,591,672 B2 | 11/2013 | Janko et al. |
| 8,790,393 B2 | 7/2014 | Bregulla et al. |
| 8,808,618 B2 | 8/2014 | Furst et al. |
| 8,815,061 B2 | 8/2014 | Andreacchi et al. |
| 8,852,264 B2 | 10/2014 | Pacetti et al. |
| 9,045,843 B2 | 6/2015 | Andreacchi et al. |
| 9,133,563 B2 | 9/2015 | Andreacchi |
| 9,145,619 B2 | 9/2015 | Andreacchi et al. |
| 9,566,147 B2 | 2/2017 | Kramer-Brown et al. |
| 9,566,174 B1 | 2/2017 | De et al. |
| 9,592,135 B2 | 3/2017 | Thompson |
| 9,668,890 B2 | 6/2017 | Ma et al. |
| 10,441,445 B2 | 10/2019 | Kramer-Brown et al. |
| 10,617,541 B2 | 4/2020 | Nishigishi |
| 10,835,393 B2 | 11/2020 | Ma et al. |
| 11,141,296 B2 | 10/2021 | Thompson |
| 11,298,251 B2 | 4/2022 | Simpson et al. |
| 11,779,477 B2 | 10/2023 | Simpson et al. |
| 2001/0009981 A1 | 7/2001 | Dubois et al. |
| 2002/0032477 A1 | 3/2002 | Helmus et al. |
| 2002/0062092 A1 | 5/2002 | Muni et al. |
| 2002/0082524 A1 | 6/2002 | Anderson et al. |
| 2002/0087099 A1 | 7/2002 | Nanis et al. |
| 2003/0102360 A1 | 6/2003 | Eungard et al. |
| 2003/0120181 A1 | 6/2003 | Toma et al. |
| 2003/0125642 A1 | 7/2003 | Kato et al. |
| 2003/0134142 A1 | 7/2003 | Vey et al. |
| 2004/0111044 A1 | 6/2004 | Davis et al. |
| 2004/0129347 A1 | 7/2004 | Craig |
| 2004/0167436 A1 | 8/2004 | Reynolds et al. |
| 2004/0167442 A1 | 8/2004 | Shireman et al. |
| 2004/0181175 A1 | 9/2004 | Clayman et al. |
| 2004/0225231 A1 | 11/2004 | Ehr |
| 2004/0236433 A1 | 11/2004 | Kennedy et al. |
| 2004/0243168 A1 | 12/2004 | Ferrera et al. |
| 2004/0267351 A1 | 12/2004 | Swain |

(56) References Cited

U.S. PATENT DOCUMENTS

| | | |
|---|---|---|
| 2005/0054952 A1 | 3/2005 | Eskuri et al. |
| 2005/0056687 A1 | 3/2005 | Matsumoto et al. |
| 2005/0059889 A1 | 3/2005 | Mayer |
| 2005/0060025 A1 | 3/2005 | MacKiewicz et al. |
| 2005/0070997 A1 | 3/2005 | Thornton et al. |
| 2005/0096568 A1 | 5/2005 | Kato |
| 2005/0098444 A1 | 5/2005 | Schaeffer |
| 2005/0124917 A1 | 6/2005 | Skujins et al. |
| 2005/0137501 A1 | 6/2005 | Euteneuer et al. |
| 2005/0145307 A1 | 7/2005 | Shireman et al. |
| 2005/0145508 A1 | 7/2005 | Larsen et al. |
| 2005/0263171 A1 | 12/2005 | Wu et al. |
| 2005/0263717 A1 | 12/2005 | Soluri et al. |
| 2005/0267385 A1 | 12/2005 | Hofmann et al. |
| 2005/0273021 A1 | 12/2005 | Burgermeister |
| 2005/0273156 A1* | 12/2005 | Burgermeister ...... A61L 31/022 623/1.15 |
| 2005/0288773 A1 | 12/2005 | Glocker et al. |
| 2006/0079954 A1* | 4/2006 | Burgermeister ........ A61F 2/915 623/1.15 |
| 2006/0122537 A1 | 6/2006 | Reynolds et al. |
| 2006/0190070 A1 | 8/2006 | Dieck et al. |
| 2006/0241519 A1 | 10/2006 | Hojeibane et al. |
| 2006/0259126 A1 | 11/2006 | Lenz |
| 2006/0264784 A1 | 11/2006 | Lupton |
| 2006/0271169 A1 | 11/2006 | Lye et al. |
| 2006/0272751 A1 | 12/2006 | Kato |
| 2006/0287709 A1 | 12/2006 | Rao |
| 2007/0034527 A1 | 2/2007 | Diaz et al. |
| 2007/0034528 A1 | 2/2007 | Diaz et al. |
| 2007/0135891 A1 | 6/2007 | Schneider |
| 2007/0156215 A1 | 7/2007 | Jensen et al. |
| 2007/0173925 A1 | 7/2007 | Fliedner |
| 2007/0185415 A1 | 8/2007 | Ressemann et al. |
| 2007/0185564 A1 | 8/2007 | Pacetti et al. |
| 2007/0198044 A1 | 8/2007 | Lupton et al. |
| 2007/0209947 A1 | 9/2007 | Shrivastava et al. |
| 2007/0219464 A1 | 9/2007 | Davis et al. |
| 2007/0219465 A1 | 9/2007 | Cedro et al. |
| 2007/0219624 A1 | 9/2007 | Brown et al. |
| 2007/0244413 A1 | 10/2007 | Biggins |
| 2007/0249964 A1 | 10/2007 | Richardson et al. |
| 2007/0249965 A1 | 10/2007 | Abrams et al. |
| 2007/0265699 A1 | 11/2007 | Grewe et al. |
| 2007/0270942 A1 | 11/2007 | Thomas |
| 2008/0004546 A1 | 1/2008 | Kato |
| 2008/0033522 A1 | 2/2008 | Grewe et al. |
| 2008/0070058 A1 | 3/2008 | Dasgupta et al. |
| 2008/0077049 A1 | 3/2008 | Hirshman |
| 2008/0091267 A1 | 4/2008 | Stinson et al. |
| 2008/0097248 A1 | 4/2008 | Munoz et al. |
| 2008/0146967 A1 | 6/2008 | Richardson et al. |
| 2008/0160259 A1 | 7/2008 | Nielson et al. |
| 2008/0161726 A1 | 7/2008 | Yutaka |
| 2008/0177371 A1 | 7/2008 | Ryan et al. |
| 2008/0183280 A1 | 7/2008 | Agnew et al. |
| 2008/0200879 A1 | 8/2008 | Jalisi et al. |
| 2008/0208308 A1 | 8/2008 | Allen et al. |
| 2008/0208352 A1 | 8/2008 | Krivoruchko et al. |
| 2008/0215132 A1 | 9/2008 | Ryan et al. |
| 2008/0228109 A1 | 9/2008 | Kinoshita et al. |
| 2008/0234605 A1 | 9/2008 | Urie |
| 2008/0257717 A1 | 10/2008 | Vacheron |
| 2008/0262600 A1 | 10/2008 | Jalisi |
| 2008/0281230 A1 | 11/2008 | Kinoshita et al. |
| 2008/0312747 A1 | 12/2008 | Cameron et al. |
| 2009/0000105 A1 | 1/2009 | Kato |
| 2009/0030500 A1 | 1/2009 | Weber et al. |
| 2009/0048659 A1 | 2/2009 | Weber et al. |
| 2009/0093871 A1 | 4/2009 | Rea et al. |
| 2009/0112127 A1 | 4/2009 | Keating et al. |
| 2009/0118675 A1 | 5/2009 | Czyscon et al. |
| 2009/0118822 A1 | 5/2009 | Holman et al. |
| 2009/0149947 A1 | 6/2009 | Frohwitter |
| 2009/0163833 A1 | 6/2009 | Kinoshita et al. |
| 2009/0204203 A1 | 8/2009 | Allen et al. |
| 2009/0227902 A1 | 9/2009 | Simpson et al. |
| 2009/0240324 A1 | 9/2009 | Smith |
| 2009/0254000 A1 | 10/2009 | Layman et al. |
| 2009/0255827 A1 | 10/2009 | Andreacchi et al. |
| 2009/0258050 A1 | 10/2009 | Lindsay et al. |
| 2009/0259299 A1 | 10/2009 | Moloney |
| 2009/0276033 A1 | 11/2009 | Mayer |
| 2010/0004562 A1 | 1/2010 | Jalisi et al. |
| 2010/0004733 A1 | 1/2010 | Atanasoska et al. |
| 2010/0049304 A1 | 2/2010 | Clifford et al. |
| 2010/0158426 A1 | 6/2010 | Manipatruni et al. |
| 2010/0158436 A1 | 6/2010 | Riska |
| 2010/0172789 A1* | 7/2010 | Calla ..................... C23C 24/04 420/451 |
| 2010/0217373 A1 | 8/2010 | Boyle et al. |
| 2010/0222866 A1 | 9/2010 | Wachter et al. |
| 2010/0222873 A1 | 9/2010 | Atanasoska et al. |
| 2010/0241210 A1 | 9/2010 | Patadia |
| 2010/0249654 A1 | 9/2010 | Elsesser et al. |
| 2010/0262227 A1 | 10/2010 | Rangwala et al. |
| 2011/0062031 A1 | 3/2011 | Wulf |
| 2011/0066106 A1 | 3/2011 | Kato |
| 2011/0106236 A1 | 5/2011 | Su et al. |
| 2011/0118628 A1 | 5/2011 | Zhou et al. |
| 2011/0247943 A1 | 10/2011 | Bialas et al. |
| 2011/0264161 A1 | 10/2011 | Schiefer et al. |
| 2011/0319872 A1 | 12/2011 | Kawasaki |
| 2011/0319980 A1 | 12/2011 | Ryan |
| 2012/0016458 A1 | 1/2012 | Abunassar |
| 2012/0041342 A1 | 2/2012 | Purtzer |
| 2012/0065623 A1 | 3/2012 | Nelson et al. |
| 2012/0109108 A1 | 5/2012 | Boyle et al. |
| 2012/0123525 A1 | 5/2012 | Kramer-Brown et al. |
| 2012/0199489 A1 | 8/2012 | Vacheron |
| 2012/0282571 A1 | 11/2012 | Ammon et al. |
| 2013/0006149 A1 | 1/2013 | Purtzer |
| 2013/0006222 A1 | 1/2013 | Nabeshima et al. |
| 2013/0013055 A1 | 1/2013 | Pacetti et al. |
| 2013/0092554 A1 | 4/2013 | Wong et al. |
| 2013/0092556 A1 | 4/2013 | Wong et al. |
| 2013/0092557 A1 | 4/2013 | Wong et al. |
| 2013/0096669 A1 | 4/2013 | Bregulla et al. |
| 2013/0204353 A1 | 8/2013 | Kramer-Brown et al. |
| 2013/0241112 A1 | 9/2013 | Jow |
| 2014/0014530 A1 | 1/2014 | Lin |
| 2014/0076719 A1 | 3/2014 | Andreacchi et al. |
| 2014/0076720 A1 | 3/2014 | Andreacchi et al. |
| 2014/0076737 A1 | 3/2014 | Andreacchi et al. |
| 2014/0076739 A1 | 3/2014 | Andreacchi |
| 2014/0155979 A1 | 6/2014 | Lam et al. |
| 2014/0271319 A1* | 9/2014 | Zheng .................. C22C 19/002 419/9 |
| 2014/0277392 A1 | 9/2014 | Webler, Jr. |
| 2014/0360887 A1 | 12/2014 | Andreacchi et al. |
| 2016/0002816 A1 | 1/2016 | Andreacchi |
| 2017/0296365 A1 | 10/2017 | Kramer-Brown et al. |
| 2018/0340245 A1* | 11/2018 | Kernion ................ C22C 30/00 |

FOREIGN PATENT DOCUMENTS

| | | |
|---|---|---|
| CN | 102356185 A | 2/2012 |
| CN | 102481662 A | 5/2012 |
| CN | 102552991 A | 7/2012 |
| CN | 202412010 U | 9/2012 |
| CN | 103252496 A * | 8/2013 |
| CN | 110306099 A * | 10/2019 |
| EP | 0804934 A2 | 11/1997 |
| EP | 1604691 A2 | 12/2005 |
| EP | 1632584 A1 | 3/2006 |
| EP | 1674118 A2 | 6/2006 |
| EP | 1731241 A1 | 12/2006 |
| EP | 1829982 A1 | 9/2007 |
| EP | 2054101 A2 | 5/2009 |
| EP | 2640432 | 5/2012 |
| EP | 2676684 A1 | 12/2013 |
| EP | 2676686 A1 | 12/2013 |
| EP | 3138587 A1 | 8/2017 |
| JP | 07-090694 A | 4/1995 |

(56) References Cited

FOREIGN PATENT DOCUMENTS

| | | | |
|---|---|---|---|
| JP | 08-302500 A | | 11/1996 |
| JP | 09-508538 | | 9/1997 |
| JP | 10025531 A | * | 1/1998 |
| JP | 2001001124 A | * | 1/2001 |
| JP | 2002-503529 | | 2/2002 |
| JP | 2002-069555 A | | 3/2002 |
| JP | 2003-267609 A | | 9/2003 |
| JP | 2006-519068 | | 8/2006 |
| JP | 2008-188670 A | | 8/2008 |
| WO | 97/33534 A1 | | 9/1997 |
| WO | 99/15108 A2 | | 4/1999 |
| WO | 00/54704 A1 | | 9/2000 |
| WO | 00/69368 A2 | | 11/2000 |
| WO | 01/15632 A1 | | 3/2001 |
| WO | 01/17577 A1 | | 3/2001 |
| WO | 01/61080 A1 | | 8/2001 |
| WO | 01/72349 A1 | | 10/2001 |
| WO | 02/78763 | | 10/2002 |
| WO | 2007/103446 A2 | | 9/2007 |
| WO | 2008/022126 A1 | | 2/2008 |
| WO | 2009/126431 A2 | | 10/2009 |
| WO | 2010/081723 A1 | | 7/2010 |
| WO | 2010/107798 A1 | | 9/2010 |
| WO | 2012/068358 A1 | | 5/2012 |
| WO | 2013/162690 A1 | | 10/2013 |
| WO | 2014/159743 A1 | | 10/2014 |
| WO | 2014/159747 A1 | | 10/2014 |

OTHER PUBLICATIONS

Donachie et al. Chapter 7 Powder Metallurgy Processing. Superalloys A Technical Guide. Second Edition. 2002. ASM International. 117-134. (Year: 2002).*
Liu. 2 Processes and Techniques for Droplet Generation. Science and Engineering of Droplets. Notes Publications. 2000. 19-120. ( Year: 2000).*
Shang. CoCrFeNi(W1-xMox) high-entropy alloy coatings with excellent mechanical properties and corrosion resistance prepared by mechanical alloying and hot pressing sintering. Materials and Design 117 (2017) 193-202. (Year: 2017).*
Zhang et al. Phase transformations in Co—Ni—Cr—W alloys during high temperature exposure to steam environment. J. Phase Equil. Diffus. (2018) 39:387-400. (Year: 2018).*
Campbell, ed. Chapter 16 Nonequilbrium Reactions—Precipitation Hardening. Phase Diagrams Understanding the Basics. ASM International. 2012. 339-361. (Year: 2012).*
Sheng. A Co—Cr—Ni—W—C alloy processed by multiple rolling. Strength of Materials, vol. 52, No. 1, Jan. 2020. (Year: 2020).*
CN 101554685 machine translation (Year: 2009).*
CN 103252496 machine translation (Year: 2013).*
CN 110306099 machine translation (Year: 2019).*
JP 2001-001124 machine translation (Year: 2001).*
JP H10-025531 machine translation (Year: 1998).*
Poletti et al. Development of a new high entropy alloy for wear resistance: FeCoCrNiW0.3 and FeCoCrNiW0.3 + 5 at.% of C Materials and Design 115 (2017) 247-254 (Year: 2017).*
Wang et al. Microstructure and mechanical properties of CoCrFeNiWx high entropy alloys reinforced by u phase particles Journal of Alloys and Compounds 843 (2020) 155997 (Year: 2020).*
U.S. Appl. No. 11/736,979, filed Apr. 10, 2013, Issue Notification.
U.S. Appl. No. 11/736,979, filed Feb. 20, 2013, Issue Notification.
Cordis Palmaz Blue .018 Peripheral Stent System, Johson & Johnson Medical NV/SA, May 2005 (2 pages) http://www.jnordic.com/Lists/FileList1/Attatchments/174/PalmazBlue.sub.--018.sub.-Brochure. PDF.
Dinega, Dmitry P., and M. G. Bawendi. "A solution-phase chemical approach to a new crystal structure of cobalt." Angewandte Chemie International Edition 38.12 (1999): 1788-1791.
Giessen et al., "Coronary Stenting with a New Radiopaque Balloon Expandable Endoprosthesis in Pigs", Circulation, vol. 83, No. 5, May 1991, pp. 1788-1798.

Issue Notification received for U.S. Appl. No. 09/534,071, mailed on Jul. 11, 2007.
Issue Notification received for U.S. Appl. No. 13/618,602, mailed on Sep. 17, 2014.
Notice of Allowance received for U.S. Appl. No. 09/534,071, mailed on Feb. 12, 2007.
Notice of Allowance received for U.S. Appl. No. 11/736,979, mailed on Nov. 9, 2012.
Notice of Allowance received for U.S. Appl. No. 13/618,602, mailed on May 27, 2014.
Notice of Allowance received for U.S. Appl. No. 13/830,404, mailed on Oct. 18, 2016.
Notice of Allowance received for U.S. Appl. No. 15/429,339, mailed on Jun. 5, 2019.
Office Action received for U.S. Appl. No. 09/534,071, mailed on Aug. 29, 2005.
Office Action received for U.S. Appl. No. 09/534,071, mailed on Dec. 18, 2002.
Office Action received for U.S. Appl. No. 09/534,071, mailed on Mar. 13, 2006.
Office Action received for U.S. Appl. No. 09/534,071, mailed on Nov. 15, 2005.
Office Action received for U.S. Appl. No. 09/534,071, mailed on Sep. 13, 2006.
Office Action received for U.S. Appl. No. 09/534,071, mailed on Sep. 17, 2002.
Office Action received for U.S. Appl. No. 11/736,979, mailed on Apr. 4, 2011.
Office Action received for U.S. Appl. No. 11/736,979, mailed on Apr. 12, 2012.
Office Action received for U.S. Appl. No. 11/736,979, mailed on Aug. 31, 2010.
Office Action received for U.S. Appl. No. 11/736,979, mailed on May 26, 2010.
Office Action received for U.S. Appl. No. 11/736,979, mailed on Sep. 19, 2011.
Office Action received for U.S. Appl. No. 13/618,602, mailed on May 3, 2013.
Office Action received for U.S. Appl. No. 09/534,071, mailed on Jul. 9, 2003.
Office Action received for U.S. Appl. No. 13/298,070, mailed on Jun. 25, 2014.
Office Action received for U.S. Appl. No. 13/298,070, mailed on Oct. 6, 2014.
Office Action received for U.S. Appl. No. 13/618,602, mailed on Aug. 20, 2013.
Office Action received for U.S. Appl. No. 13/618,602, mailed on Jan. 6, 2014.
Office Action received for U.S. Appl. No. 13/830,404, mailed on Apr. 20, 2016.
Office Action received for U.S. Appl. No. 13/830,404, mailed on Aug. 10, 2016.
Office Action received for U.S. Appl. No. 13/830,404, mailed on Jan. 8, 2016.
Office Action received for U.S. Appl. No. 13/830,404, mailed on May 29, 2015.
Office Action received for U.S. Appl. No. 13/830,404, mailed on Sep. 16, 2015.
Office Action received for U.S. Appl. No. 15/429,339, mailed on Feb. 26, 2019.
Ohring et al. "A Versatile Arc Melting Apparatus for Quenching Molten Metals and Ceramics." Review of Scientific instruments 42.4 (1971): 530-531.
Restriction Requirement received for U.S. Appl. No. 13/618,602, mailed on Mar. 4, 2013.
Restriction Requirement received for U.S. Appl. No. 13/298,070, mailed on May 2, 2014.
U.S. Appl. filed Nov. 17, 2010, Boylan., U.S. Appl. No. 61/414,566.
U.S. Patent Application filed on Mar. 14, 2013, by Kramer-Brown et al., U.S. Appl. No. 13/830,404.
Final Office Action received for U.S. Appl. No. 16/601,259, mailed on Sep. 23, 2021, 11 pages.

(56) References Cited

OTHER PUBLICATIONS

Non-Final Office Action received for U.S. Appl. No. 16/601,259, mailed on May 17, 2021, 11 pages.
Notice of Allowance received for U.S. Appl. No. 16/601,259, mailed on Dec. 6, 2021, 8 pages.
Notice of Allowance received for U.S. Appl. No. 16/601,259, mailed on Mar. 9, 2022, 6 pages.
Narushima, Precipitates-in-Biomedical-Co—Cr—Alloys_Narushima-Mineta-Kurihara-Ueda_Publishedonline-Feb. 26,2013, Feb. 26, 2013, JOM, vol. 65, No. 4, 2013, 489, 65.
U.S. Appl. No. 13/618,455, filed Sep. 14, 2012, Andreacchi et al.
U.S. Appl. No. 13/618,455, Mail Date May 13, 2015, Issue Notification.
U.S. Appl. No. 13/618,455, filed May 8, 2014, Office Action.
U.S. Appl. No. 13/618,455, filed Sep. 25, 2014, Office Action.
Advisory Action received for U.S. Appl. No. 15/670,761, mailed on Jan. 12, 2022, 3 pages.
Advisory Action received for U.S. Appl. No. 15/670,761, mailed on Mar. 16, 2021, 3 pages.
Duerig, T. W., Melton, K. N., & Stockel, D. (2013), Engineering aspects of shape memory alloys. Butterworth-Heinemann, 414-419.
Eutectic system. In Wikipedia, The Free Encyclopedia. Retrieved 11:54, Apr. 27, 2010, 1-5, from https://en.wikipedia.org/w/index.php?title=Eutectic_system&oldid=702728275.
Final Office Action received for U.S. Appl. No. 15/670,761, mailed on Jan. 27, 2021, 13 pages.
Final Office Action received for U.S. Appl. No. 15/670,761, mailed on Oct. 29, 2021, 15 pages.
Forging of Niobium, tantalum, and their alloys, MetalPass, accessed Apr. 18, 2013. http://www.metalpass.com/metaldoc/paper.aspx?docID=312.
Gold. (Mar. 3, 2016). In Wikipedia, The Free Encyclopedia. Retrieved 11:55, Apr. 27, 2010, 1-24, from https://en.wikipedia.org/w/index.php?title=Gold&oldid=708000804.
Gold. In Wikipedia, The Free Encyclopedia. Revised on Apr. 22, 2010, Retrieved 11:11, Aug. 7, 2017, 1-21, from https://en.wikipedia.org/w/index.php?title=Gold&diff=357659233&oldid=357425502.
Indium. In Wikipedia, The Free Encyclopedia. Retrieved 12:13, Apr. 27, 2010, 1-7, from https://en.wikipedia.org/w/index.php?title=Indium&oldid=706790732.
International Search Report and Written Opinion of the International Searching Authority dated Sep. 26, 2007, for related PCT Application No. PCT/US2007/05844.
Issue Notification received for U.S. Appl. No. 13/172,278 mailed on Jul. 19, 2017.
Issue Notification received for U.S. Appl. No. 13/548,908 mailed on Mar. 11, 2015.
Jacobson, D. M., & Humpston, G, (1989). Gold coatings for fluxless soldering. Gold Bulletin, 22(1), 9-18.
Non-Final Office Action received for U.S. Appl. No. 15/670,761, mailed on Jul. 20, 2021, 14 pages.
Non-Final Office Action received for U.S. Appl. No. 15/670,761, mailed on Jun. 1, 2022, 11 pages.
Non-Final Office Action received for U.S. Appl. No. 15/670,761, mailed on Oct. 15, 2020, 14 pages.
Notice of Allowance received for U.S. Appl. No. 12/100,991 mailed on Aug. 17, 2012.
Notice of Allowance received for U.S. Appl. No. 13/172,278 mailed on Apr. 11, 2017.
Notice of Allowance received for U.S. Appl. No. 13/548,908 mailed on Dec. 2, 2014.
Notice of Allowance received for U.S. Appl. No. 13/617,877, mailed on May 28, 2015.
Notice of Allowance received for U.S. Appl. No. 13/618,348 mailed on Aug. 6, 2014.
Notice of Allowance received for U.S. Appl. No. 14/466,513, mailed on Mar. 28, 2017.
Notice of Allowance received for U.S. Appl. No. 11/370,642 mailed on Apr. 12, 2010.
Notification of Transmittal of the International Search Report and the Written Opinion of the International Searching Authority, or the Declaration, Patent Cooperation Treaty, European Patent Office, Dec. 29, 2009 (12 pages).
Office Action received for U.S. Appl. No. 11/370,642 mailed on Sep. 22, 2009.
Office Action received for U.S. Appl. No. 12/100,991 mailed on Dec. 21, 2011.
Office Action received for U.S. Appl. No. 12/100,991 mailed on Sep. 29, 2011.
Office Action received for U.S. Appl. No. 13/172,278 mailed on Apr. 3, 2015.
Office Action received for U.S. Appl. No. 13/172,278 mailed on Jun. 10, 2013.
Office Action received for U.S. Appl. No. 13/172,278 mailed on Nov. 21, 2013.
Office Action received for U.S. Appl. No. 13/172,278 mailed on Oct. 8, 2015.
Office Action received for U.S. Appl. No. 13/172,278 mailed on Sep. 19, 2016.
Office Action received for U.S. Appl. No. 13/548,908 mailed on Jun. 18, 2014.
Tin. In Wikipedia, The Free Encyclopedia. Retrieved 12:08, Apr. 27, 2010, 1-15, from https://en.wikipedia.org/w/index.php?title=Tin&oldid=708568728.
U.S. Appl. No. 11/370,642, filed Apr. 12, 2010, Notice of Allowance.
U.S. Appl. No. 11/370,642, filed Sep. 22, 2009, Office Action.
U.S. Appl. No. 13/271,869, filed Apr. 1, 2013, Office Action.
U.S. Appl. No. 13/271,869, filed Apr. 26, 2013, Office Action.
U.S. Appl. No. 13/271,869, filed Jul. 9, 2014, Issue Notification.
U.S. Appl. No. 13/271,869, filed Mar. 18, 2014, Notice of Allowance.
U.S. Appl. No. 13/271,869, filed Nov. 27, 2013, Office Action.
U.S. Appl. No. 13/617,877, filed Dec. 20, 2013, Office Action.
U.S. Appl. No. 13/617,877, filed Sep. 14, 2012, Anthony S. Andreacchi, Sep. 23, 2014, Office Action.
U.S. Appl. No. 13/618,348, filed Dec. 19, 2013, Office Action.
U.S. Appl. No. 13/618,348, filed Sep. 14, 2012, Anthony S. Andreacchi, Aug. 6, 2014, Issue Notification.
U.S. Appl. No. 13/618,348, Mail Date Apr. 16, 2014, Notice of Allowance.
U.S. Appl. No. 13/618,407, Dec. 2, 2014, Office Action.
U.S. Appl. No. 13/618,407, Mail Date May 13, 2015, Notice of Allowance.
U.S. Appl. No. 13/618,455, filed Feb. 2, 2015, Notice of Allowance.

* cited by examiner

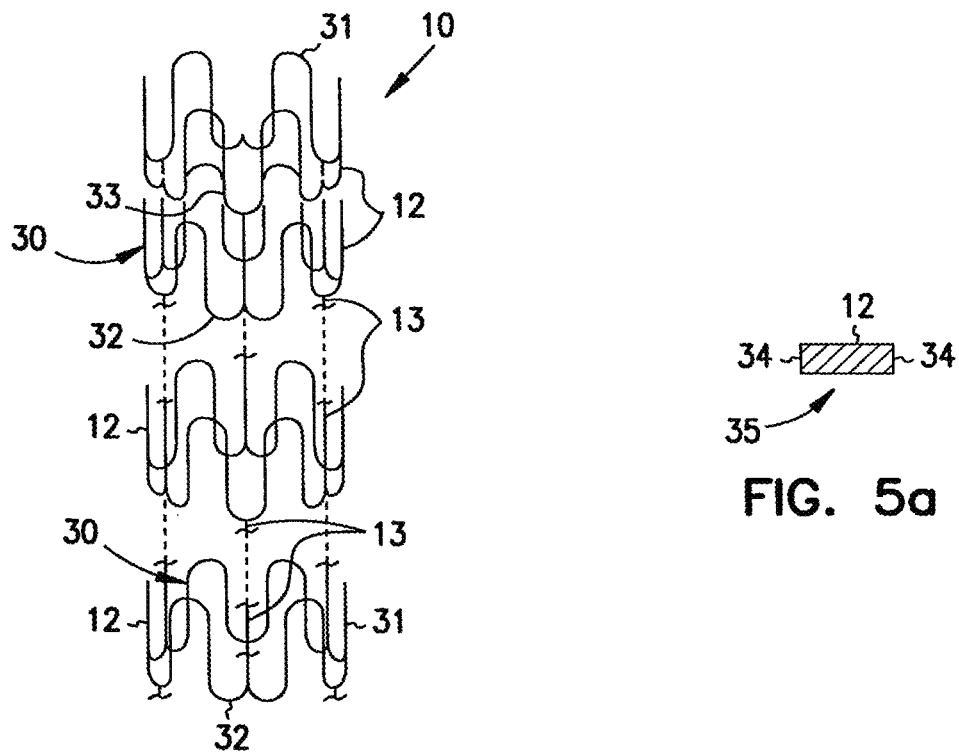
FIG. 4
FIG. 5a
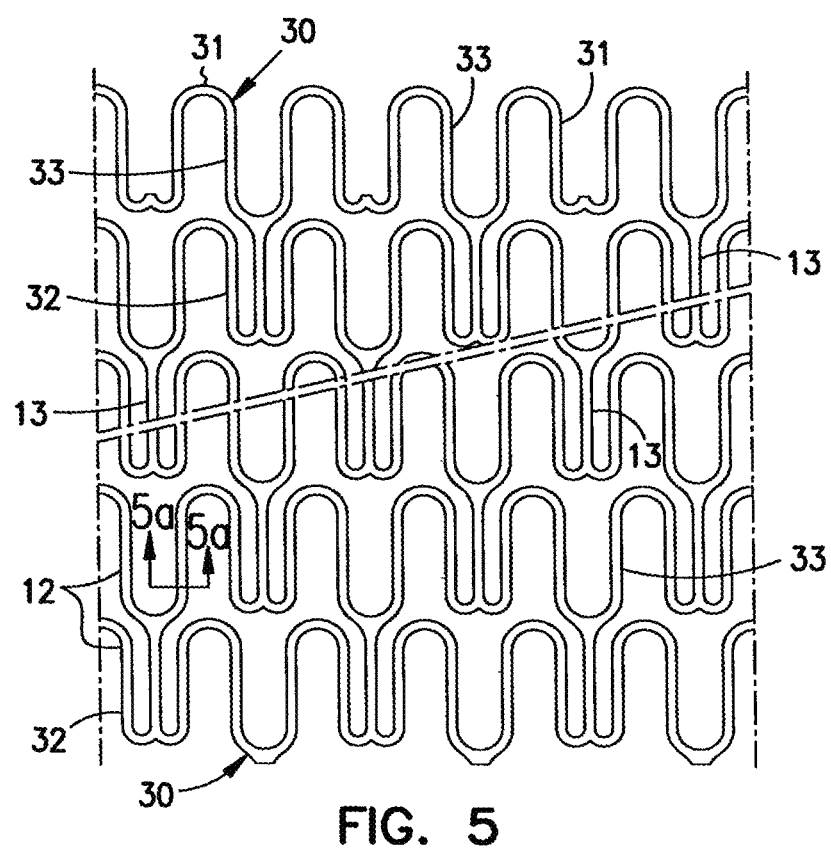
FIG. 5

METHODS FOR MANUFACTURING RADIOPAQUE INTRALUMINAL STENTS COMPRISING COBALT-BASED ALLOYS WITH SUPERSATURATED TUNGSTEN CONTENT

CROSS-REFERENCE TO RELATED APPLICATIONS

This application claims the benefit of and priority to U.S. Provisional Patent Application No. 62/914,806 (WN 17066.141) filed Oct. 14, 2019, which is herein incorporated by reference in its entirety. Application 62/914,806 and the present application each also incorporates by reference in its entirety, another application by Applicant, U.S. patent application Ser. No. 16/601,259 (WN 17066.70.1.1.1.1) filed Oct. 14, 2019.

BACKGROUND

Intraluminal stents implanted with percutaneous methods have become a standard adjunct to procedures such as balloon angioplasty in the treatment of atherosclerotic disease of the arterial system. Stents, by preventing acute vessel recoil, improve long-term patient outcome and have other benefits such as securing vessel dissections.

Intraluminal stents comprise generally tubular-shaped devices that are constructed to hold open a segment of a blood vessel or other anatomical lumen. Intraluminal stents are used in treatment of diseases such as atherosclerotic stenosis as well as diseases of the stomach and esophagus, and for urinary tract applications. Adequate stent function requires a precise placement of the stent over a lesion or site of plaque or other lumen site in need of treatment. Typically, the stent is delivered to a treatment site by a delivery catheter that comprises an expandable portion for expanding the stent within the lumen.

The delivery catheter onto which the stent is mounted may be a balloon delivery catheter similar to those used for balloon angioplasty procedures. In order for the stent to remain in place on the balloon during delivery to the site of damage within a lumen, the stent may be compressed onto the balloon. The catheter and stent assembly is introduced within a patient's vasculature using a guide wire. The guide wire is disposed across the damaged arterial section and then the catheter-stent assembly is advanced over the guide wire within the artery until the stent is directly within the lesion or the damaged section.

The balloon of the catheter is expanded, expanding the stent against the artery wall. The artery is preferably slightly expanded by the expansion of the stent to seat or otherwise fix the stent to prevent movement. In some circumstances during treatment of stenotic portions of the artery, the artery may have to be expanded considerably in order to facilitate passage of blood or other fluid therethrough. In the case of a self expanding stent, the stent is expanded by retraction of a sheath or actuation of a release mechanism. Self expanding stents may expand to the vessel wall automatically without the aid of a dilation balloon, although such a dilation balloon may be used for another purpose.

These manipulations are performed within the body of a patient by a practitioner who may rely upon both placement markers on the stent catheter and on the radiopacity of the stent itself. The stent radiopacity arises from a combination of stent material and stent pattern, including stent strut or wall thickness. After deployment within the vessel, the stent radiopacity should allow adequate visibility of both the stent and the underlying vessel and/or lesion morphology under fluoroscopic visualization.

Stent radiopacity relies on the use of materials having high density, a high atomic number and/or a high electron density contrast compared to the stent's surroundings. Prior art materials used for this purpose typically include platinum group metals and other precious or exotic metals, which come with complex supply chain issues, and high cost. Alternative materials and combinations have been explored previously, but often suffer from unacceptable radiopacity, defects in microstructure, and other manufacturing challenges.

SUMMARY

In particular, many proposed alloys are not stable as a single-phase material during manufacture and fail to avoid the occurrence of a multiphase microstructure with a second phase having a large particle size and that is poorly distributed within the material, which can lead to problems during processing steps such as heating, drawing, cutting and electropolishing. For example, the occurrence of a locally concentrated second phase with large particle sizes can lead to selective attack of one phase at the expense of another, and leads to difficulties in controlling mechanical performance properties of the resulting stent.

A need therefore continues to exist for stent alloys that achieve enhanced radiopacity without using a platinum group metal or other precious or exotic metals as radiopacifiers, while limiting the occurrence of a second phase to a finely dispersed second phase with a small particle size throughout manufacturing, processing, and use. The present invention thus relates to a primarily face centered cubic (FCC) cobalt-based radiopaque alloy (e.g., a Co—Cr—Ni—W alloy) including either a single-phase microstructure or a limited second phase that is finely dispersed within the alloy, to a radiopaque intraluminal stent comprised of the alloy and to methods for making the radiopaque alloy and radiopaque intraluminal stent.

One embodiment of the present invention includes a method for making a radiopaque alloy, e.g., for use in manufacturing a stent or other implantable device. In an embodiment, the cobalt-based alloy is one which increases radiopacity as compared to L-605 by increasing tungsten content, but in a way that ensures no more than 10% volume fraction of a second phase, preferably no more than 5% volume fraction of a second phase, or no more than about 16 weight percent of a second phase, preferably no more than about 8 weight percent of a second phase, such that the alloy is maintained primarily as face-centered-cubic (FCC), even above the normal solubility limit of tungsten in such a solid solution. Such an alloy may not replace any of the nickel present in L-605 with another element, but may maintain such nickel (e.g., at about 10% by weight), even in light of any allergy concerns, in order to ensure austenitic stability, and FCC phase stability, even at super-saturated tungsten content.

Tungsten ordinarily causes separation into two phases in a cobalt-chromium alloy at concentrations above 15% tungsten by weight. By processing the alloy during manufacture in a particular manner, it is possible to increase the tungsten content above this threshold, while at the same time maintaining the desired content of a primarily single-phase FCC crystalline structure by limiting the particle size and volume fraction or weight percent of any second phase particles. Such a primarily single-phase structure provides advantageous and desired mechanical and physical properties (e.g., avoidance of segregated, brittle intermetallic phases such as $Co_3W$ and the like) as compared to what would normally occur in Co—Cr alloys with elevated tungsten content as a result of the tungsten causing separation into two coarse phases or formation of a second phase with a large particle size, while at the same time delivering increased radiopacity as a result of the elevated tungsten content, all while maintaining the super-saturated tungsten content in a primarily single-phase FCC structure with only extremely fine particles of a second phase. Tungsten may be elevated to a super-saturated level, such as up to about 35% by weight of the alloy, or such as about 20-35% by weight of the alloy. Supersaturation may be attained by heating to form a solid solution and then quickly cooling to avoid formation of a second phase or using powder metallurgy processes with rapid cooling rates to create very fine powders of the alloy that limit the formation of a second phase and the size of second phase particles.

In addition to various other techniques that will be apparent to one of skill in the art in light of the present disclosure, one technique that could be used to provide such rapid cooling rates, to result in the desired structure, may include physical vapor deposition ("PVD"). When using a PVD technique, material can be deposited at the atomic level, where solid material is vaporized in a controlled environment. Such a PVD process has rapid cooling rates and atomic level deposition, which enables one to achieve the desired fine microstructure. Deposition can be in the form of tube, sheet, or other predefined shape, with a particle size upper limit of, e.g., ~20 microns (e.g., less than 20 µm, less than 15 µm, less than 10 µm, less than 5 µm or any of the other µm values described herein). Such particle size values may be for the average particle size exhibited (e.g., average particle size of less than 20, less than 15, less than 10, or less than 5 µm), or may mean that no particles are present that are larger than such size.

An important advantage of PVD as compared to powder metallurgy or splat/ribbon cooling techniques is that the material buildup mechanism in PVD involves no liquid-to-solid transformation with attendant solubility changes and tendency for phase separation. Due to its atom by atom buildup onto a solid substrate, PVD can produce essentially homogeneous compositions, even where the system's phase diagram might predict formation of multiple phases if the same compositional system were processed via traditional ingot metallurgy. Further, if PVD is used to build up an alloy as described herein including tungsten in excess of 15% by weight directly onto a cylindrical substrate, the as-deposited tube could have a homogeneous, essentially single phase microstructure, even without the need for performing an elevated temperature heat treatment followed by rapid quench.

The maintenance of the primarily single-phase FCC crystalline structure in the alloy with elevated tungsten can optionally allow for age hardening, which controls the separation of phases such that any second phase exists only as extremely fine particles. By using specific temperature and time parameters, the alloy may be strengthened through the formation of extremely fine precipitates of $Co_3W$ while preserving the advantages of the primarily single-phase material with super-saturated tungsten content.

The alloy may be used to form a radiopaque stent. The radiopaque stent comprises a cylindrical main body, where the body is formed (e.g., entirely) from the Co—Cr alloy with super-saturated tungsten content, while maintaining a primarily single-phase FCC microstructure.

Methods for making such stents are also disclosed. The method may comprise providing a tube comprising the Co—Cr alloy with supersaturated tungsten content, but in a primarily single-phase FCC microstructure. The tube can be shaped to form a radiopaque stent.

The alloy may include chromium (e.g., in a concentration of about 20% by weight), and nickel in a concentration of 5-15% by weight (e.g., about 10% by weight), as well as small quantities of manganese (e.g., in a concentration of 0-5% by weight), iron (e.g., in a concentration of 0-5% by weight), as well as other trace elements in a concentration of 1% maximum, 0.5% maximum, 0.3% maximum, 0.2% maximum, 0.1% maximum, 0.05% maximum, or 0.01% maximum. Exemplary trace elements may include silicon (e.g., up to about 0.2%), phosphorus (up to about 0.02%), and sulfur (up to about 0.02%). Other trace elements typically present in an L-605 alloy (e.g., beryllium, boron, carbon) may be absent, or at least present at lower concentration than the L-605 standard permits. According to a further embodiment of the radiopaque Co—Cr—Ni—W alloy of the present invention, the alloy is substantially free of molybdenum, carbon and/or other elements not mentioned as included, as deliberate alloying elements. The phrase "substantially free" as used herein may include less than 0.05%, less than 0.04%, less than 0.03%, less than 0.02%, less than 0.01% or preferably 0% by weight. The alloy of course also includes tungsten in a concentration above its solubility limit in a cobalt-chromium alloy, such as at 20-35% by weight, but is processed in a manner to ensure that the alloy is of a primarily homogeneous single-phase with only extremely fine and uniformly dispersed particles of a second phase (e.g., FCC, primarily single-phase solid solution). The phrase "primarily single-phase" as used herein may include less than 10% volume fraction of a second phase, less than 7%, less than 5% or less than 3% (e.g., up to about 2%), or less than about 16 weight percent of a second phase, less than 14 weight percent, less than 10 weight percent, less than 8 weight percent, less than 6 weight percent or less than 4 weight percent (e.g., up to about 3 weight percent), wherein the particles of the second phase have a maximum or even average particle size of 0.5 µm to 5 µm, including a maximum or average particle size of 3 µm. Any such second phase is finely dispersed, e.g., with a maximum or average particle size that may be less than 10% of the wall thickness of the stent wall. For example, where the wall thickness may be 50 to 100 µm, or 75 to 100 µm, maximum or even average particle size of any finely dispersed second phase may be less than 10% that of the wall thickness (e.g., 15 µm or less, 10 µm or less, 5 µm or less, 4 µm or less, 3 µm or less, 2 µm or less, or even 1 µm or less) so that the presence of any such second phase has a minimal impact on desired mechanical properties. Again, a primarily homogeneous single-phase structure is attained by heating into a molten form to about at least 1300° C., about at least 1400° C. or about at least 1500° C. followed by rapid cooling, such as by using powder metallurgy processes with rapid cooling rates to create very fine powders of the alloy that limit the formation of a second phase and the size of second phase particles.

The balance of the alloy is cobalt, e.g., about 30 to 50% by weight. As tungsten content increases, it may substitute for reduced cobalt content. For example, where 20% by weight tungsten is included, cobalt may be at about 45 to 50%, or 46 to 48%. Where 25% by weight tungsten is included cobalt may be at about 5 percentage points lower (e.g., 40 to 45%, or 41 to 43% by weight). Similarly, at 30% by weight tungsten, cobalt may be another 5 percentage points lower (e.g., 35 to 40%, or 36 to 38% by weight). At 35% by weight tungsten, which is extremely super-saturated in tungsten content, cobalt may be another 5 percentage points lower (e.g., 30% to 35%, or 31 to 33% by weight). In an embodiment, the sum of cobalt and tungsten content may be about 65-70%, or 66-68% by weight. In an embodiment including 20% tungsten, the tungsten/cobalt weight percent ratio (W/Co) may be about from 0.35 to 0.5, or from 0.4 to about 0.45, in an embodiment including 25% tungsten, the W/Co ratio may be from about 0.5 to 0.7, or from about 0.57 to 0.63. In an embodiment including 30% tungsten, the W/Co ratio may be from about 0.7 to about 0.9, or from 0.79 to 0.85, and in an embodiment including 30% tungsten, the W/Co ratio may actually be 1 or greater, such as from 1 to 1.2, or from 1.07 to 1.13.

In an embodiment, the alloy may comprise no more than 1%, no more than 0.5%, no more than 0.4%, no more than 0.3%, no more than 0.2%, no more than 0.1%, no more than 0.05%, no more than 0.03%, or no more than 0.02% of any of silicon, phosphorous or sulfur by weight.

In an embodiment, the alloy may include, or consist essentially of cobalt, chromium, nickel and tungsten. The alloy (including a solution from which it is formed) may not include any other alloying elements in amounts greater than 3%, or 2%, by weight.

Features from any of the disclosed embodiments may be used in combination with one another, without limitation. For example, any of the compositional limitations described with respect to one embodiment (e.g., limited iron content, limited content of other elements, or the like) may be present in any of the other described embodiments. Further, the content of nickel may be increased so as to enhance the stability of the FCC structure and thereby potentially reducing the temperature required to attain the homogeneous primarily single-phase structure prior to quenching. In addition, other features and advantages of the present disclosure will become apparent to those of ordinary skill in the art through consideration of the following detailed description and the accompanying drawings.

BRIEF DESCRIPTION OF THE DRAWINGS

To further clarify the above and other advantages and features of the present disclosure, a more particular description will be rendered by references to specific embodiments thereof, which are illustrated in the appended drawings. It is appreciated that these drawings depict only typical embodiments of the invention and are therefore not to be considered limiting of its scope. The present disclosure will be described and explained with additional specificity and detail through the use of the accompanying drawings.

FIG. 4 is a perspective view of a configuration of a radiopaque stent that can be formed according to the present invention, in an unexpanded state, with one end of the stent being shown in an exploded view to illustrate the details thereof.

FIG. 5 is a plan view of a flattened section of a radiopaque stent configuration which can be formed according to the present invention, which illustrates an undulating pattern of the stent shown in FIG. 4.

FIG. 5a is a sectional view taken along the line 5a-5a in FIG. 5.

DETAILED DESCRIPTION

I. Introduction

One aspect of the present invention is directed to an implantable radiopaque device, such as a stent, that is formed of a radiopaque cobalt-chromium-nickel-tungsten (Co—Cr—Ni—W) alloy, in which the tungsten content is specifically elevated above its normal solubility limit in cobalt-chromium, but in a way to ensure that the alloy maintains a primarily single-phase, FCC microstructure. While tungsten typically separates into two phases at concentrations of about 15% by weight at typically employed thermal processing conditions, conditions employed according to the present disclosure allow elevated tungsten concentrations, e.g., from 20-35% tungsten by weight, while maintaining primarily or substantially a single phase structure. By increasing the amount of tungsten in the alloy while retaining a primarily single-phase, FCC microstructure, the alloy enables a stent with a higher radiopacity without the use of high cost platinum group metals or precious metals, or other refractory metals, while maintaining advantageous mechanical properties, chemical processing behavior and corrosion performance associated with a single-phase material.

The alloy may undergo further processing, such as compaction, sintering, use of an isostatic press, and/or age hardening, without a reduction in radiopacity and without the creation of a coarse second phase. Compaction, sintering and isostatic pressing may be employed for creating a billet, analogous to an as cast ingot, from a fine powder resulting from powder metallurgy processes. Powder metallurgy may be particularly advantageous in methods according to the present disclosure, due to the high rate of cooling and small particle size, which reduce the occurrence of a second phase in the alloy. Age hardening includes a thermal treatment performed within a range of intermediate temperatures, which enable sufficient diffusion for tiny particles of a second phase to precipitate from a super saturated microstructure. This technique is sometimes used to boost strength and hardness in a variety of alloy systems. A particular combination of temperature, and time is determined experimentally in order to achieve a desired balance of properties. At a given ageing temperature there exists a ageing time at which strength and hardness are maximized. At shorter times the precipitates have not grown to an optimum size to impede the movement of dislocations, whereas at longer times the precipitates have become too large to be optimally effective. Appropriately aged precipitates are typically too small to be resolved by optical microscopy. Their extremely fine size make the resulting microstructure less prone to selective attack of either phase during electropolishing or general corrosion compared to traditional thermal processing of the same alloy composition.

II. Radiopaque Stents with Single-Phase Super-Saturated Tungsten Content

Figure 1:
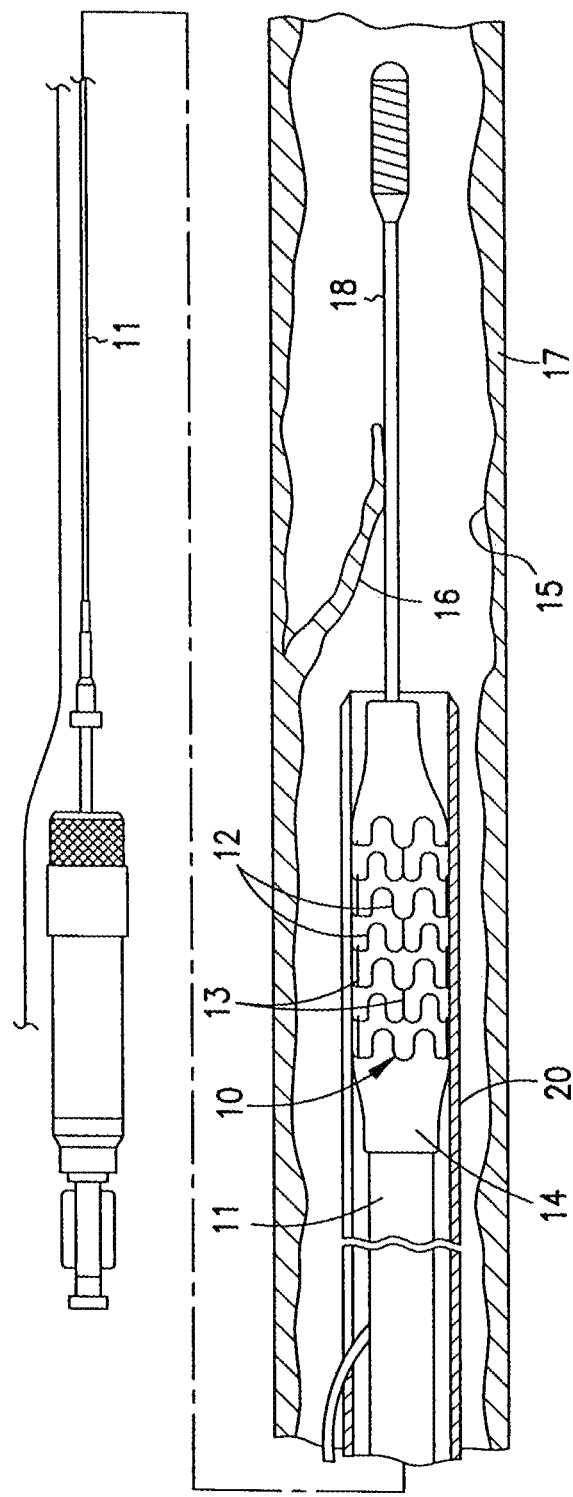
FIG. 1 is an elevational view, partially in section, of a radiopaque stent that can be formed according to the present invention, mounted on a delivery catheter and disposed within a damaged lumen.

The radiopaque stent of the present invention comprises a main body, one embodiment of which is illustrated generally at 10 in FIG. 1, which is fabricated from an alloy comprising cobalt-chromium-nickel-tungsten (Co—Cr—Ni—W) in a primarily single-phase FCC microstructure. The Co—Cr—Ni—W alloy is fabricated using up to 35% tungsten by weight, for example 20-35%, but in a manner that retains a primarily single-phase FCC microstructure, which is capable of deforming in a ductile manner, rendering the radiopaque stent of the present invention expandable.

The radiopaque Co—Cr—Ni—W alloy may be similar to L-605, but in which the amount of tungsten is increased to 20-35% by weight, or up to 35% by weight, while the remaining weight fractions of other alloying elements in L-605 may remain unaltered (other than cobalt, which decreases). For example, alloy L-605 contains 15% by weight tungsten. By increasing the amount of tungsten to up to 35% by weight, or 20-35% by weight, (by substituting some of the cobalt), while retaining the remaining weight fractions, the relative radiopacity of the resulting alloy is increased relative to L-605, and where care is taken during manufacture to quickly quench the alloy, the resulting alloy can advantageously have a primarily single-phase, FCC microstructure. It will be appreciated that many other alloys that may nominally include such fractions of tungsten will not necessarily include the required primarily single-phase FCC structure, but will include a coarse, tungsten rich second phase (e.g. $Co_3W$ due to the elevated tungsten content) and/or a plurality of microcrystalline phases, due to the elevated tungsten content. At an elevated temperature (e.g., at about at least 1300° C., about at least 1400° C. or about at least 1500° C.), a single-phase FCC structure can be achieved in such Co—Cr alloys, and if care is taken in ensuring that cooling of the alloy occurs quickly, with sufficient austenitic stabilization content (e.g., Ni and Mn), it is possible to preserve a primarily single-phase alloy in which the tungsten (and the other alloying elements) continue to primarily exhibit the FCC crystalline structure, rather than forming two coarse phases, as would be typical.

Using powder metallurgy processes according to the present disclosure may include forming a single-phase alloy melt of the composition and subsequently spraying the single-phase alloy melt as quick cooling droplets through a nozzle (e.g. droplets smaller than about 25 μm), pouring the single-phase alloy melt against a spinning drum to create a fine ribbon, or related techniques. Where the cooling of the melt is rapid as described herein, the desired structure with primarily FCC characteristics can be formed. The alloy melt must be completely molten and may require superheat to counteract heat losses by the feed system and the nozzle, such that the processes include heating the alloy melt to an elevated temperature of about at least 1300° C., about at least 1400° C. or about at least 1500° C. prior to rapid cooling (e.g. 200 to 500° C./s). The resulting fine particles have a maximum or even average particle size of less than 15 μm, such as from 0.5 μm to 10 μm and form a powder which may then be compacted, sintered and optionally processed in a hot isostatic press to form a powder metallurgy billet analogous to a cast ingot. The billet may then be processed in essentially the same manner as a cast ingot.

Hot isostatic pressing subjects the powder to both an elevated temperature and isostatic gas pressure in a high-pressure containment vessel, and may be adapted to achieve a minimum of 99.5% dense alloy. High sintering temperatures of about 1200 to 1300° C. may be used to enable high diffusion rates for promoting powder bonding and void reduction. As the billets may be subsequently wrought into tubing or wire, additional densification may be achieved thereby. If needed, cooling following such hot isostatic pressing may be carried out as described herein, to result in quick cooling, maintaining the desired primarily single phase structure.

Age hardening of an alloy according to the present disclosure allows further improvement of the mechanical properties of the material, without a reduction in radiopacity or formation of a coarse second phase within the microstructure.

Another technique that could be used to provide the desired rapid cooling rate, and result in the desired structure, may include physical vapor deposition ("PVD"). When using a PVD technique, material can be deposited at the atomic level, where solid material is vaporized in a controlled environment. Such a PVD process has rapid cooling rates and atomic level deposition, which enables one to achieve the desired fine microstructure. Deposition can be in the form of tube, sheet, or other predefined shape, with a particle size upper limit of, e.g., ~20 microns (e.g., less than 20 μm, less than 15 μm, less than 10 μm, less than 5 μm or any of the other μm values described herein). Such particle size values may be for the average particle size exhibited (e.g., average particle size of less than 20, less than 15, less than 10, or less than 5 μm), or may mean that no particles are present that are larger than such size.

An important advantage of PVD as compared to powder metallurgy or splat/ribbon cooling techniques is that the material buildup mechanism in PVD involves no liquid-to-solid transformation with attendant solubility changes and tendency for phase separation. Due to its atom by atom buildup onto a solid substrate, PVD can produce essentially homogeneous compositions, even where the system's phase diagram might predict formation of multiple phases if the same compositional system were processed via traditional ingot metallurgy. Further, if PVD is used to build up an alloy as described herein including tungsten in excess of 15% by weight directly onto a cylindrical substrate, the as-deposited tube could have a homogeneous, essentially single phase microstructure, even without the need for performing an elevated temperature heat treatment followed by rapid quench.

One embodiment of the radiopaque Co—Cr—Ni—W alloy of the present invention is comprised of chromium in a concentration of about 20% (e.g., 15% to 25%) by weight, tungsten in a concentration that is greater than 15% (e.g., at least 20%, such as 20-35% by weight, nickel in a concentration of 5-15% (e.g., about 10%) by weight, manganese in a concentration of 0-5% (e.g., 1-3%) by weight, and iron in a concentration of 0-5% (e.g., 0-3%, or 1-3%) by weight. Trace elements may be present, if at all, in concentrations of less than 1%, less than 0.5%, less than 0.4%, less than 0.3%, less than 0.2%, less than 0.1%, less than 0.05%, less than 0.04%, less than 0.03%, less than 0.02%, or less than 0.01% by weight. The balance of material is cobalt, e.g., about 30-50% by weight. In an embodiment, the weight fractions for one or more of chromium, manganese, iron, or nickel may be identical to those in L-605. In an embodiment, the fractions of cobalt and tungsten may be the only difference in composition relative to L-605, although the sum of the cobalt+tungsten weight fractions may be equal to that of L-605 (e.g., 66-68% by weight).

According to a further embodiment of the radiopaque Co—Cr—Ni—W alloy, the alloy may be substantially or entirely free of molybdenum and/or carbon as deliberately added alloying elements. "Substantially free" as used herein may include less than 0.05%, less than 0.04%, less than 0.03%, less than 0.02%, or less than 0.01% weight. The alloy may also be free or substantially free of any other elements of the periodic table not specifically noted as present herein.

According to a further embodiment, the alloy comprises no more than 1%, no more than 0.5%, no more than 0.4%, no more than 0.3%, or no more than 0.2% of silicon. The alloy may be substantially free of phosphorous and/or sulfur, as quantified above (e.g., no more than 0.02% by weight of each).

The radiopaque stent of the present invention overcomes limitations and weaknesses of other stents, e.g., particularly L-605 stents, which exhibit less than ideal radiopacity, without requiring addition of relatively expensive alloying elements, such as platinum, palladium, iridium, or the like, while at the same time ensuring that the stent can be formed from a homogenous material (no coatings, various metallic layers, markers or the like), in which the alloy exhibits a primarily single-phase FCC microstructure, but with supersaturated tungsten content. Such a stent imparts a more visible image when absorbing x-rays during fluoroscopy as compared to a dimensionally similar L-605 stent, while providing other advantages over alternative stent alloys that employ expensive alloying elements. With this more visible image, the entire stent is better observed by the practitioner placing the stent. The image observed by the practitioner is not "washed out" due to excessive brightness and is not too dim. Because of the improved image, the stent is accurately positioned and manipulated within a lumen of a patient, with a radiopacity such that stent expansion during and after deployment may be assessed accurately by the practitioner. An additional advantage to the increased radiopacity is the visualization of the stent and the underlying vessel during follow-up examinations by the practitioner.

Because the entire stent is radiopaque, the diameter and length of the stent are readily discerned by the practitioner. Also, because the stent itself is made of the radiopaque alloy, the stent does not have problems associated with radiopaque coatings or varying metallic layers, such as cracking or separation or corrosion. Also, because the entire stent is radiopaque, the stent does not require extra markers with their attendant issues.

The low profile of the Co—Cr—Ni—W stent, coupled with its enhanced radiopacity renders the stent more easily deliverable with easier observation and detection throughout its therapeutic use than stents heretofore available, at a lower cost. A stent constructed of a Co—Cr—Ni—W alloy as contemplated herein can be made thinner than one of stainless steel without sacrificing fluoroscopic visibility and can be free from costly platinum group metals, precious metals, and other relatively expensive exotic metals (e.g., the platinum group metals, precious metals and refractory metals other than tungsten noted in Applicant's U.S. Pat. Nos. 10,441,445; 9,566,147; Ser. Nos. 16/601,259; 13/298,070; and 61/414,566, each of which is herein incorporated by reference in its entirety). The low profile of the Co—Cr—Ni—W stent renders the stent more deliverable with greater flexibility.

Furthermore, the use of a Co—Cr—Ni—W alloy that includes 20-35% tungsten by weight in a primarily single-phase composition results in improved radiopacity of the low profile stent of the present invention over prior art cobalt chromium alloys using lesser amounts of tungsten as a radiopacifier, and increases deliverability of the stent and offers significant performance advantages regarding decreasing the fluid mechanical disturbances of blood flow. Improved radiopacity assists the practitioner in placing the device precisely. Inflation or other deployment of the stent is better monitored because the stent is better visible to the practitioner. This visibility reduces the incidence and probability of an under-deployed stent. Further, in-stent restenosis is monitored as the stent and an injected contrast agent are able to be imaged simultaneously. Unlike some stents, the stent of the present invention does not produce an image which is too bright, thereby obscuring imaging of the underlying vessel morphology.

While cobalt chromium alloys containing up to 15% by weight tungsten, such as L-605, have been used in many applications, these alloys are unable to replicate the improved radiopacity achieved with platinum group metals and other precious metals known in the art. The composition of L-605 is as follows.

TABLE 1

ASTM F90 L-605 Alloy

| Element | Weight Percent | Atomic Percent |
| --- | --- | --- |
| Cobalt | 53.4 | 53.9 |
| Chromium | 20 | 24.4 |
| Tungsten | 15 | 5.2 |

TABLE 1-continued

ASTM F90 L-605 Alloy

| Element | Weight Percent | Atomic Percent |
|---|---|---|
| Nickel | 10 | 10.8 |
| Manganese (maximum) | 1.5 | 2.3 |
| Iron (maximum) | 0.1 | 3.4 |

L-605 is reported to have a melting range of 1602 to 1683K (e.g., 1329 to 1410° C.) a maximum hardness of 277 HB and a density of 9.13 g/cm$^3$. This alloy in annealed bar form has a minimum ultimate tensile strength of 125 ksi, a minimum yield strength of 45 ksi and a minimum total elongation of 30%. While many of these properties are desirable, and suitable for stent manufacture, the relative radiopacity of L-605 is lacking, e.g., being only 3.6 barnes/cc. While this is better than stainless steel (with a relative radiopacity of only about 2.5 barnes/cc), it is far below a more suitable range, such as greater than 4 barnes/cc, greater than 4.5 barnes/cc, or from 4 barnes/cc to 10 barnes/cc, 4 barnes/cc to 8 barnes/cc, or 4 barnes/cc to 7 barnes/cc.

Variations in the level of tungsten in the cobalt chromium alloy L-605, and by extension in the radiopacity of the alloy, have previously been restricted to 15% by weight, due to the solubility limits of tungsten in such Co—Cr alloys, as well as other restraints. As shown in FIGS. 17a-18c, attempts to increase tungsten past the solubility limit, according to known methods in the prior art, results in multiple coarse phases (rather than primarily a single FCC phase with a finely distributed second phase) leading to loss of desirable mechanical properties of the L-605 microstructure and alloy. According to FIGS. 17a-c, an increased tungsten content of 20% leads to an unacceptably large second phase of Co$_3$W that is concentrated in the material. At a level of 25% tungsten the second phase becomes even more pervasive, as illustrated in a comparison of FIGS. 17a-c with FIGS. 18a-c. The loss of a primarily single-phase austenitic microstructure in an alloy with supersaturated levels of tungsten impairs the mechanical properties of the alloy and can cause material weaknesses, e.g. due to the stress concentrations caused by the presence of the coarse second phase particles. These large particles are further subject to selective attack during processing and should be avoided.

It has not previously been possible to increase the level of tungsten in the alloy to 20-35% without losing the advantages of a single-phase austenitic microstructure, or at least a primarily single-phase austenitic microstructure. This is due at least in part to the low solubility limit of tungsten within the alloy at usage temperatures, and the tendency for increased levels of tungsten in the alloy to induce the formation of a coarse multiphase microstructure. This coarse multiphase microstructure is subject to selective attack, and exhibits decreased mechanical properties. Tungsten is actually a HCP stabilizer, not an FCC stabilizer and is known to form coarse phases of Co$_3$W and Co$_7$W$_6$. Course phases of such are to be avoided, within the present embodiments.

While some attempts have been made to improve the radiopacity of L-605, these strategies have generally relied on the use of expensive and exotic elements, sometimes with the simultaneous replacement of nickel. Even where such may increase radiopacity, they can result in a decrease in other desirable mechanical properties and may not result in a primarily single-phase microstructure. Further, the inherent expense may be cost prohibitive in a competitive business environment.

Materials having a coarse multiphase microstructure are prone to defects in processing and are disadvantageous for use in stent products. Of particular concern is the tendency of high levels of tungsten to cause segregation in the initial as cast material. During heat treatment care must be taken to achieve substantially complete homogeneity. Appropriate processes for maintaining a high homogeneity in the alloy requires the use of high temperatures in the solution and rapid cooling by quenching or using powder metallurgy processes.

The currently described embodiments having 20-35% tungsten have been found to improve the radiopacity of the material to comparable levels achieved by alloys relying on platinum group metals or other exotic metals addition, but without compromising the primarily single-phase, FCC microstructure that is one advantage of an otherwise inferior L-605 alloy. In addition, tungsten is relatively abundant and inexpensive as compared to many alternative proposed radiopacity increasing alloying metals.

Figure 11:
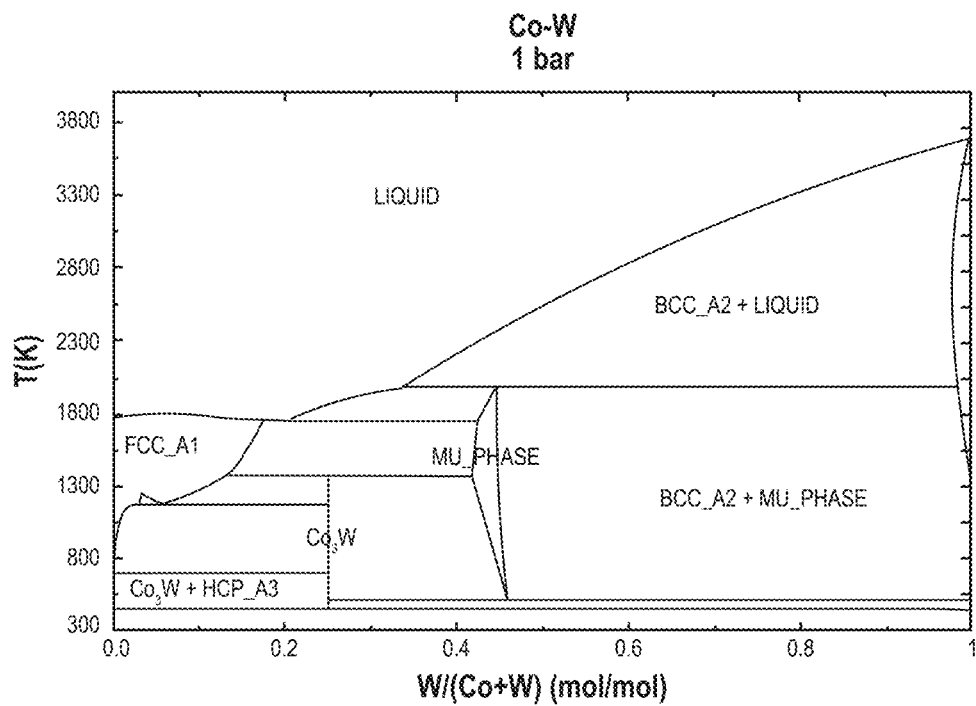
FIG. 11 shows a phase diagram for cobalt-tungsten.
Figure 12:
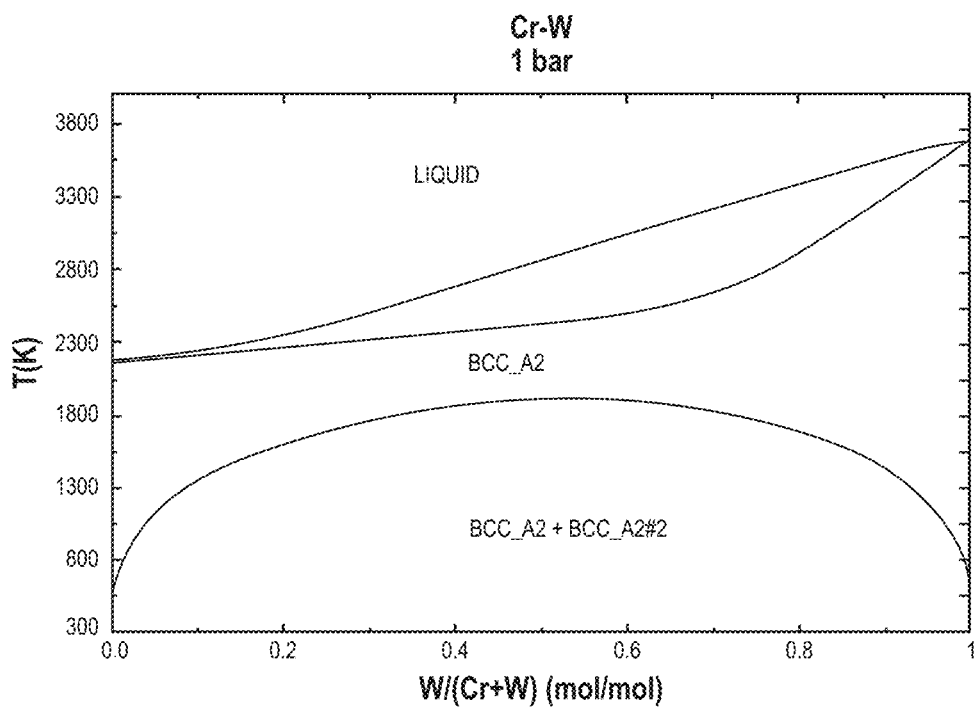
FIG. 12 shows a phase diagram for chromium-tungsten.
Figure 13:
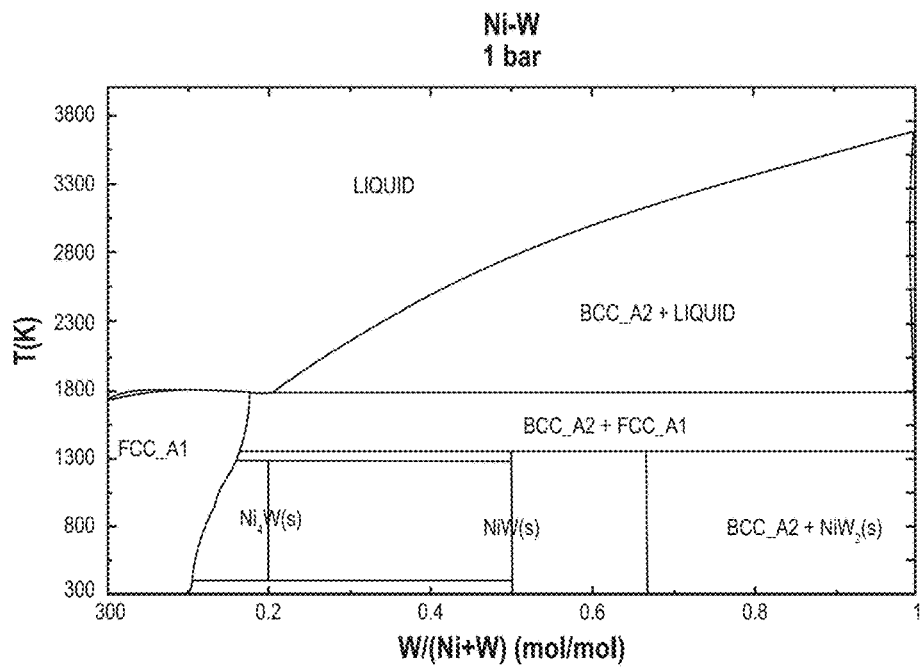
FIG. 13 shows an additional phase diagram for nickel-tungsten.
Figure 14:
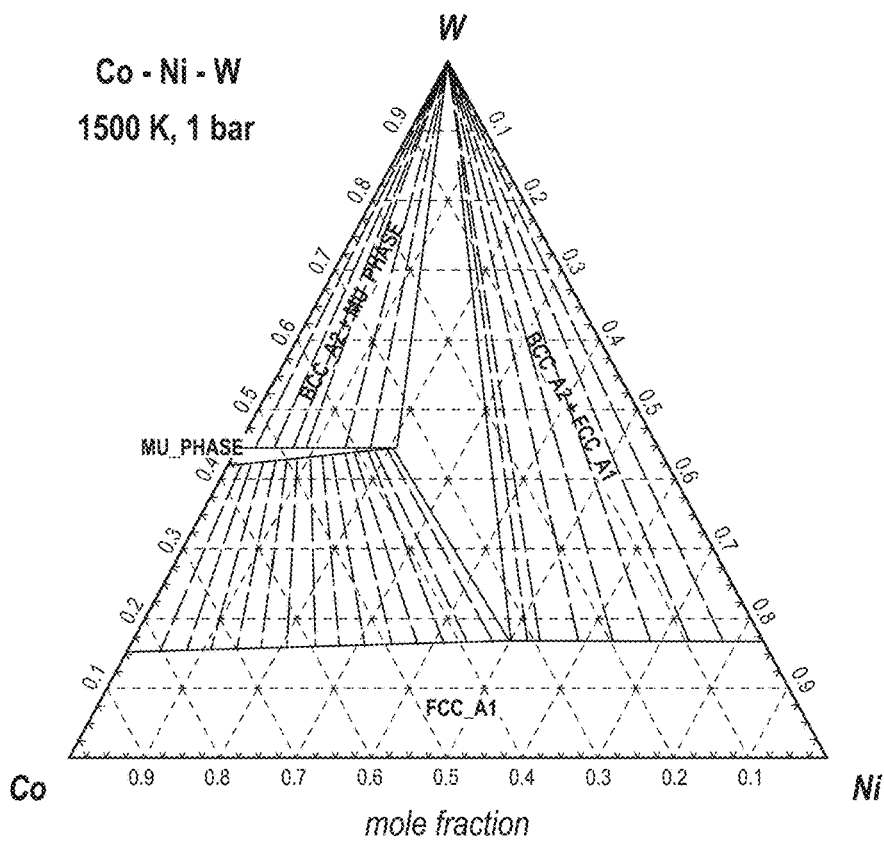
FIG. 14 shows a ternary phase diagram for cobalt-nickel-tungsten at 1500K.
Figure 15:
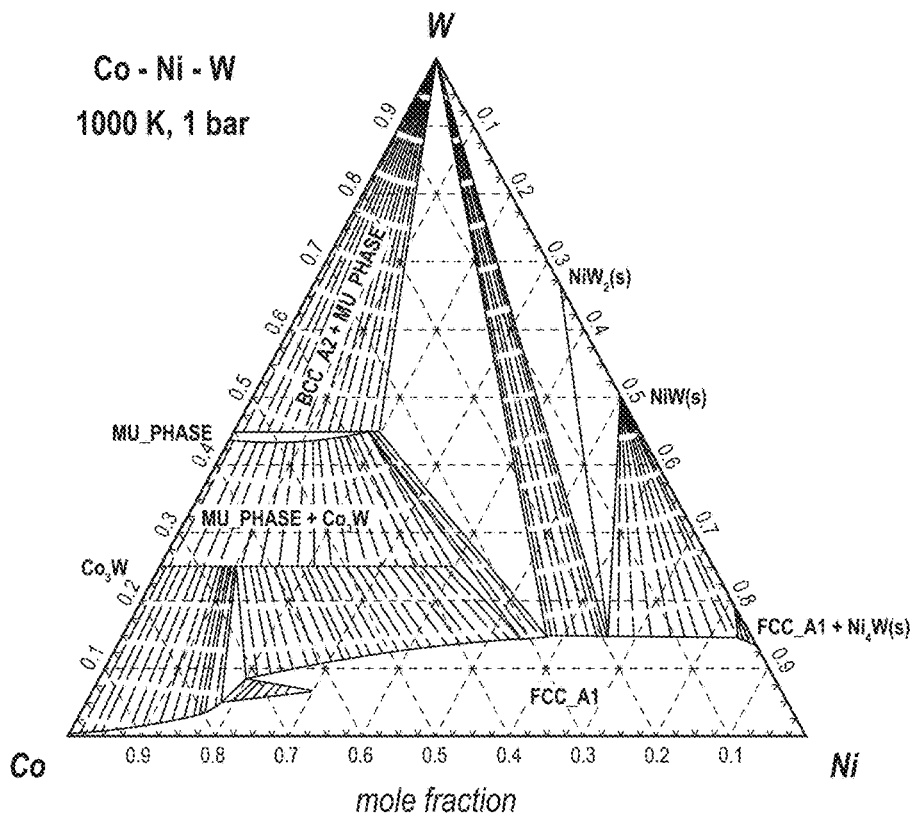
FIG. 15 shows a ternary phase diagram for cobalt-nickel-tungsten at 1000K.
Figure 16:
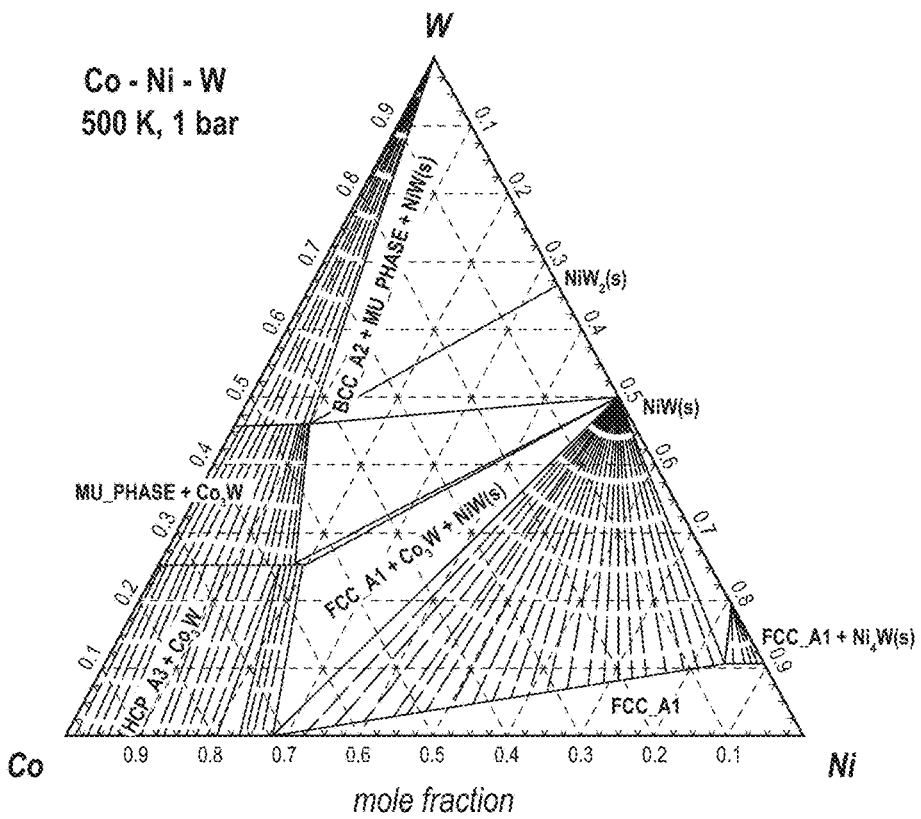
FIG. 16 shows a ternary phase diagram for cobalt-nickel-tungsten at 500K.
Figure 17A:
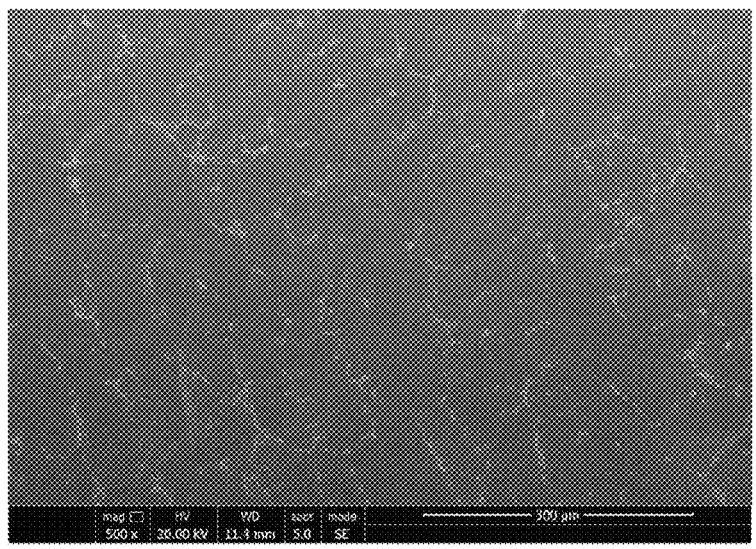
FIG. 17a shows an SEM image of an as cast ingot of a Co—Cr—Ni—W alloy having 20% W content and a coarse second phase.
Figure 17B:
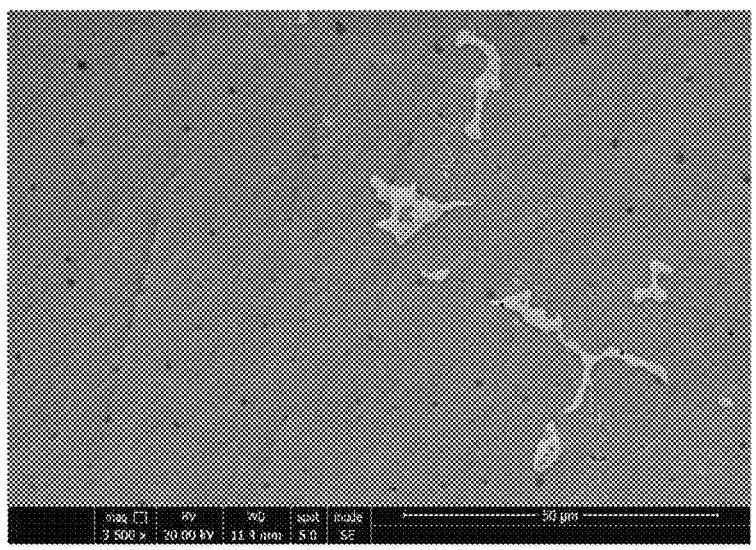
FIG. 17b shows an SEM image of a Co—Cr—Ni—W alloy according to FIG. 17a at an increased resolution.
Figure 17C:
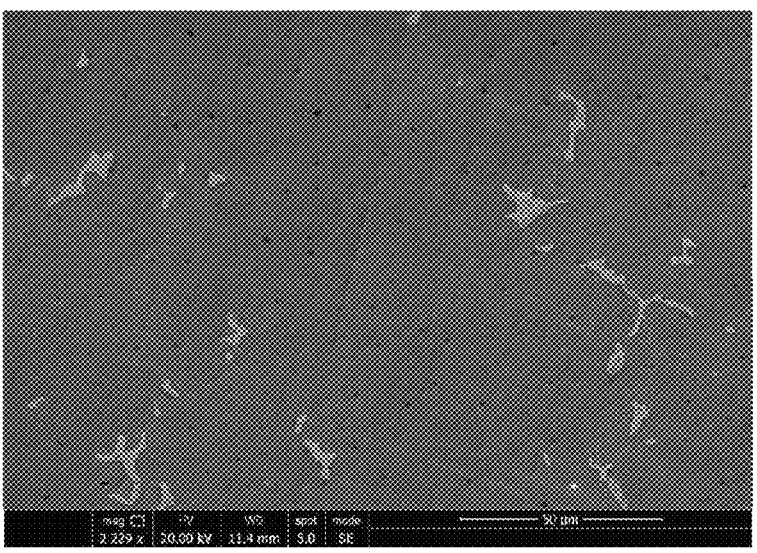
FIG. 17c shows an SEM image of a Co—Cr—Ni—W alloy according to FIG. 17a at an increased resolution.
Figure 18A:
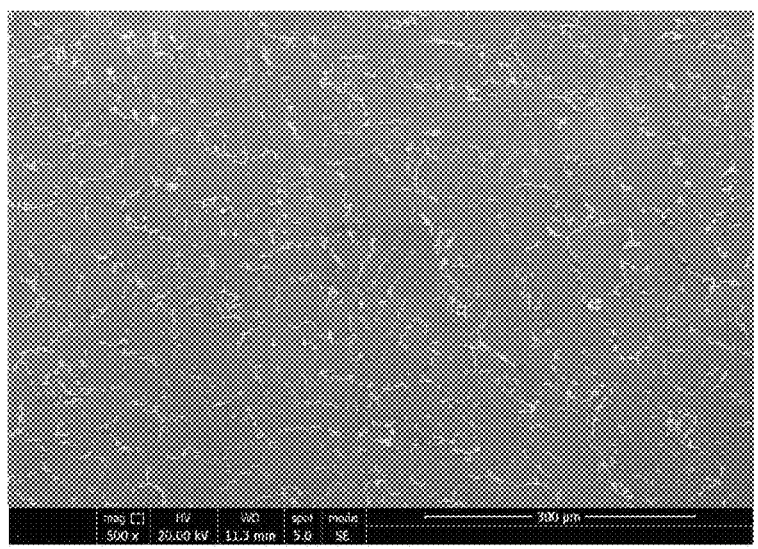
FIG. 18a shows an SEM image of an as cast ingot of a Co—Cr—Ni—W alloy having 25% W content and a coarse second phase.
Figure 18B:
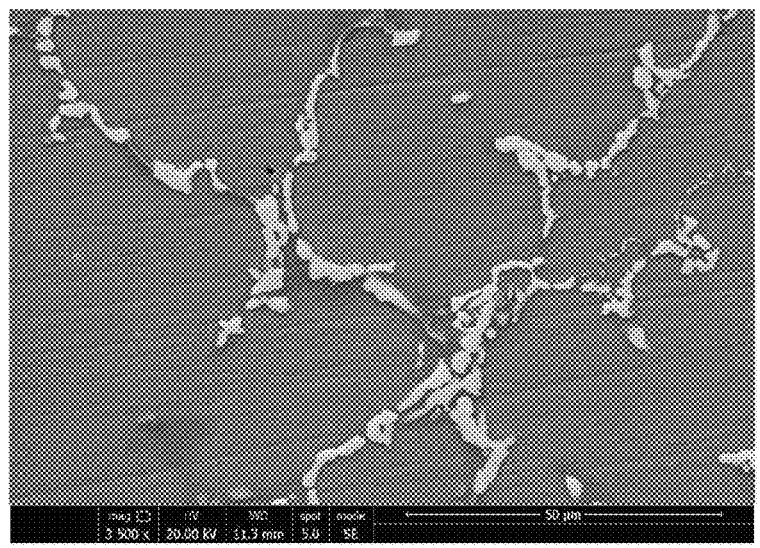
FIG. 18b shows an SEM image of a Co—Cr—Ni—W alloy according to FIG. 18a at an increased resolution.
Figure 18C:
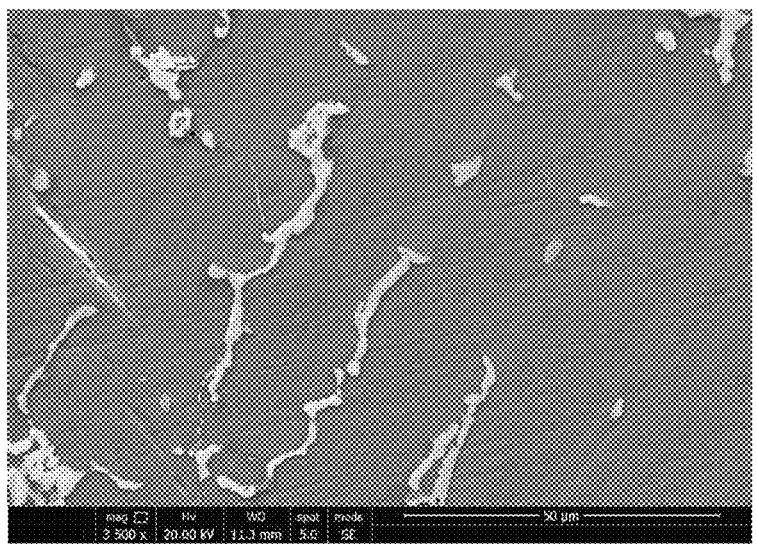
FIG. 18c shows an SEM image of a Co—Cr—Ni—W alloy according to FIG. 18a at an increased resolution.

To form a Co—Cr—Ni—W alloy having 20-35% tungsten according to one embodiment of the present disclosure, each of the principal elements (i.e., cobalt, chromium, nickel and tungsten) can be refined to form a furnace charge stock that is combined in an alloy melt and cast as ingots. The refined principal elements are combined in solution at a high temperature of at least about 1500K, (e.g., 1227° C.), under which conditions the solubility limit of tungsten in the solution is increased significantly, and to achieve homogenization of the elements in a single phase or primarily single-phase FCC microstructure. FIGS. 14-16 show how such Co—Cr—Ni—W alloys exhibit greater equilibrium solubility of the tungsten at elevated temperatures (e.g., at about 1500K), and that this equilibrium solubility drops significantly at 500K (it is similarly low at ambient temperature (e.g., 293K)). FIGS. 11-13 show simple binary phase diagrams for Co—W, Cr—W, and Ni—W, respectively. In order to achieve good homogenization of the elements at the elevated temperature (e.g., at least about 1500K), the process may include maintaining the solid solution at said temperature for a given period of time in order to ensure the desired uniform homogenous distribution of tungsten and the other alloying elements throughout the solution. For example, the solution may be maintained at said temperature for at least about 1 minute, at least about 2 minutes, at least about 3 minutes, at least about 5 minutes, from 1 minute to 200 minutes, from 1 minute to 100 minutes, from 1 minute to about 60 minutes, or from 1 to 30 minutes. Such a dwell time at the elevated temperature also ensures that the solution has sufficient time to reach the equilibrium state in which the single-phase FCC structure is attained. The solution is cooled from the relatively high processing temperature to about 500K or less (e.g., 227° C.), within a short time period (e.g., less than 10 minutes, less than 5 minutes, less than 4 minutes, less than 3 minutes, less than 2 minutes, or less than 1 minute), in order to keep high levels of tungsten trapped in solution with a primarily single-phase FCC microstructure, and to prevent the tungsten from precipitating out of the single-phase alloy (particularly as large particles), which would result in formation of a second phase of uncontrolled size. Rapid cooling of the solution may thus maintain the supersaturated composition with regards to tungsten in the alloy.

According to one embodiment of the disclosure, an alloy melt of the Co—Cr—Ni—W alloy having 20-35% tungsten may undergo rapid cooling according to powder metallurgy processes or ribbon cooling. In a powder metallurgy process, the alloy melt may be forced through a nozzle for forming fine droplets that can be cooled within a shorter time period than that achievable by quenching. In an example, the nozzle may be adapted for forming droplets smaller than 25 µm (e.g., 20 µm, 15 µm, 10 µm, 5 µm or less). A resulting powder including a primarily single-phase alloy according to the disclosure may then be processed by compaction, sintering and optionally isostatic pressing to form an alloy billet. The alloy billet may then be processed in a manner analogous to an as cast ingot.

Hot isostatic pressing subjects the powder to both an elevated temperature and isostatic gas pressure in a high-pressure containment vessel, and may be adapted to achieve a minimum of 99.5% dense alloy. High sintering temperatures of about 1200 to 1300° C. may be used to enable high diffusion rates for promoting powder bonding and void reduction. As the billets may be subsequently wrought into tubing or wire, additional densification may be achieved thereby.

In ribbon cooling the alloy melt may be poured against a drum spinning at a high speed. In an embodiment, the drum may be cooled (e.g., including coolant flow, or otherwise actively cooled). A resulting fine ribbon has a small size, that is subjected to a higher rate of cooling than is possible using quenching techniques, such that the formation of a second phase is limited in the resulting alloy.

Advantageously, the nickel, and optionally manganese, of the Co—Cr—Ni—W alloy serve as austenitic stabilizers within the solution and aid in preserving the desired primarily single-phase, FCC microstructure during the rapid cooling step, despite the amount of tungsten being above its solubility limit at room temperature. For this reason, it can be important in such embodiments where a primarily single-phase FCC microstructure is desired, to not substitute any of the 10% by weight nickel content already present in a comparative L-605 alloy. For example, nickel suppresses cobalt's allotropic transformation from a face-centered-cubic ("FCC") crystal structure (where it is stable at high temperatures) to a hexagonal-close-packed ("HCP") structure (where it is stable at low temperatures). These characteristics are apparent from FIGS. 11-16. In pure cobalt, this transformation naturally occurs at around 422° C. The addition of nickel significantly reduces cobalt's transformation temperature, thereby favoring the FCC structure, which in general, is a more ductile and more creep-resistant crystal structure than HCP. The rapid cooling of the alloy solution serves to trap the tungsten in the favored FCC structure, minimizing or eliminating formation of any substantial amounts of HCP structure.

While existing processing methods for some L-605 materials may generally adapt some temperature considerations to balance control of carbide formation in the alloy material with the desired mechanical properties of the final material, up to now, no consideration has been given to the processing that would be required to maintain a primarily single-phase, FCC microstructure in a Co—Cr—Ni—W alloy with 20-35 weight percent tungsten, paired with other compositional characteristics as shown in Examples 1-4. As some embodiments of the current Co—Cr—Ni—W alloys may be substantially or entirely free of carbon, the temperatures and cooling times of the processing described herein may be directly focused on the incorporation and homogenization of tungsten into the alloy solution with a primarily single-phase, FCC microstructure, rather than any considerations related to potential carbide formation.

By so processing the alloy, it is expected that it is possible to incorporate tungsten in the Co—Cr—Ni—W alloy material at 20-35% by weight (far above its room temperature solubility limit) while retaining the critical feature of a primarily single-phase FCC microstructure. The increased level of tungsten increases the radiopacity of the alloy material without the need for platinum group metals or other precious or expensive, exotic metals. According to one embodiment, the Co—Cr—Ni—W alloy is completely free of platinum group metals, precious metals, or other expensive elements such as platinum, palladium, ruthenium, rhodium, osmium, iridium, hafnium, rhenium, tantalum, niobium, molybdenum, zirconium, silver, gold or combinations thereof. While iron and/or manganese may be present, they each may represent no more than 3%, or no more than 2% (e.g., 1.5% by weight) of the alloy. The alloy may also be free, or substantially free of other elements of the periodic table not specifically listed in Examples 1-4.

The resulting alloys are advantageously stable and capable of additional homogenization and refining, such as age hardening, without a loss of radiopacity or the benefits of a primarily single-phase microstructure. In order to achieve the advantages of a very fine second phase from age hardening, the process may include an additional heating step following the rapid cooling or quenching of the primarily single-phase solution. For example, the resultant primarily single-phase FCC material may be heated at 600 to 1000° C., 600 to 800° C., or 600 to 675° C. for at least about 1 hour, at least about 4 hours, at least about 8 hours, at least about 16 hours, from 1 hour to 256 hours, or from 1 hour to 16 hours. Aging for the described time periods at the described temperatures ensures that the material has sufficient time to form a very fine second phase of fine particulate $Co_3W$. The austenitic stabilization of the material advantageously prevents significant formation of HCP structure, which would result in formation of multiple phases, while allowing the formation of fine particulate $Co_3W$ which impedes the movement of dislocations or defects within the microstructure of the material. The age hardening can be configured to impart a particular yield strength to the material, according to the envisioned use, without causing any tangible effect on the advantageous radiopacity and mechanical properties of the single-phase supersaturated tungsten alloy.

Known methods for processing L605 alloys generally do not employ powder metallurgy or age hardening, as there was no apparent perceived commercial advantage in doing so. Prior to the discoveries of the current disclosure, powder metallurgy was perceived as a costly method that provided insufficient benefit in material properties. However, according to the current disclosure, powder metallurgy methods for forming an L605 alloy having increased levels of tungsten can reduce the occurrence of a disadvantageous second phase, such that the second phase is limited to no more than 10% volume fraction of a second phase, preferably no more than 5% volume fraction of a second phase. The resultant second phase further may be well dispersed, e.g., having a maximum or even average particle size of 0.5 µm to 5 µm and improves the yield strength of the material. In one embodiment, the alloy of the current disclosure may have a yield strength of 45 ksi or 310 MPa.

For some embodiments of the method, the components of the Co—Cr—Ni—W alloy may be combined in an alloy melt by vacuum induction melting. Final refining may be performed in a vacuum arc remelt furnace. Homogenization may be performed to eliminate segregation, while the cooling step may include quenching the alloy solution with water, another liquid (e.g., oil) and/or a suitable gas, or cooling through powder metallurgy methods or ribbon cooling as described herein.

For some embodiments, the radiopaque stent of the present invention is fabricated from a single tube of Co—Cr—Ni—W alloy subjected to chemical etching, laser machining, conventional machining, electronic discharge machining (EDM), ion milling, slurry jet, or electron beam treatment or combinations of these treatments. For other embodiments, the stent is fabricated from wire elements of Co—Cr—Ni—W alloy that are welded together. For additional embodiments, the stent is fabricated from flat stock and is patterned, then rolled and welded. For other embodiments, the stent is fabricated from near-net shape processing such as metal injection molding.

Experimental results illustrate the possibility of creating a radiopaque Co—Cr—Ni—W alloy having 20-35% tungsten by weight, as shown by Examples 1-4 below.

Example 1

| Atomic # | Symbol | Name | Atomic Wt | Weight % | Atomic % |
|---|---|---|---|---|---|
| 1 | H | Hydrogen | 1.00794 | 0.00 | 0.00 |
| 5 | B | Boron | 10.811 | 0.00 | 0.00 |
| 6 | C | Carbon | 12.0107 | 0.00 | 0.00 |
| 7 | N | Nitrogen | 14.0067 | 0.00 | 0.00 |
| 8 | O | Oxygen | 15.9994 | 0.00 | 0.00 |
| 14 | Si | Silicon | 28.0855 | 0.20 | 0.47 |
| 15 | P | Phosphorous | 30.97376 | 0.02 | 0.04 |
| 16 | Si | Sulfur | 32.065 | 0.02 | 0.03 |
| 24 | Cr | Chromium | 51.9961 | 20.00 | 25.31 |
| 25 | Mn | Manganese | 54.93805 | 1.50 | 1.80 |
| 26 | Fe | Iron | 55.845 | 1.50 | 1.77 |
| 27 | Co | Cobalt | 58.9332 | 46.76 | 52.21 |
| 28 | Ni | Nickel | 58.6934 | 10.00 | 11.21 |
| 74 | W | Tungsten | 183.84 | 20.00 | 7.16 |
| 77 | Jr | Iridium | 192.217 | 0.00 | 0.00 |
| 78 | Pt | Platinum | 195.084 | 0.00 | 0.00 |
| 103 | Lr | Lawrencium | 262 | 0.00 | 0.00 |
| | | Total | | 100.00 | 100.00 |
| | | W/Co | | 0.43 | 0.14 |

Example 2

| Atomic # | Symbol | Name | Atomic Wt | Weight % | Atomic % |
|---|---|---|---|---|---|
| 1 | H | Hydrogen | 1.00794 | 0.00 | 0.00 |
| 5 | B | Boron | 10.811 | 0.00 | 0.00 |
| 6 | C | Carbon | 12.0107 | 0.00 | 0.00 |
| 7 | N | Nitrogen | 14.0067 | 0.00 | 0.00 |
| 8 | O | Oxygen | 15.9994 | 0.00 | 0.00 |
| 14 | Si | Silicon | 28.0855 | 0.20 | 0.47 |
| 15 | P | Phosphorous | 30.97376 | 0.02 | 0.04 |
| 16 | Si | Sulfur | 32.065 | 0.02 | 0.03 |
| 24 | Cr | Chromium | 51.9961 | 20.00 | 25.31 |
| 25 | Mn | Manganese | 54.93805 | 1.50 | 1.80 |
| 26 | Fe | Iron | 55.845 | 1.50 | 1.77 |
| 27 | Co | Cobalt | 58.9332 | 41.76 | 48.47 |
| 28 | Ni | Nickel | 58.6934 | 10.00 | 11.21 |
| 74 | W | Tungsten | 183.84 | 25.00 | 9.30 |
| 77 | Ir | Iridium | 192.217 | 0.00 | 0.00 |
| 78 | Pt | Platinum | 195.084 | 0.00 | 0.00 |
| 103 | Lr | Lawrencium | 262 | 0.00 | 0.00 |
| | | Total | | 100.00 | 100.00 |
| | | W/Co | | 0.60 | 0.19 |

Example 3

| Atomic # | Symbol | Name | Atomic Wt | Weight % | Atomic % |
|---|---|---|---|---|---|
| 1 | H | Hydrogen | 1.00794 | 0.00 | 0.00 |
| 5 | B | Boron | 10.811 | 0.00 | 0.00 |
| 6 | C | Carbon | 12.0107 | 0.00 | 0.00 |
| 7 | N | Nitrogen | 14.0067 | 0.00 | 0.00 |
| 8 | O | Oxygen | 15.9994 | 0.00 | 0.00 |
| 14 | Si | Silicon | 28.0855 | 0.20 | 0.47 |
| 15 | P | Phosphorous | 30.97376 | 0.02 | 0.04 |
| 16 | Si | Sulfur | 32.065 | 0.02 | 0.03 |
| 24 | Cr | Chromium | 51.9961 | 20.00 | 25.31 |
| 25 | Mn | Manganese | 54.93805 | 1.50 | 1.80 |
| 26 | Fe | Iron | 55.845 | 1.50 | 1.77 |
| 27 | Co | Cobalt | 58.9332 | 36.76 | 44.42 |
| 28 | Ni | Nickel | 58.6934 | 10.00 | 11.21 |
| 74 | W | Tungsten | 183.84 | 30.00 | 11.62 |
| 77 | Ir | Iridium | 192.217 | 0.00 | 0.00 |
| 78 | Pt | Platinum | 195.084 | 0.00 | 0.00 |
| 103 | Lr | Lawrencium | 262 | 0.00 | 0.00 |
| | | Total | | 100.00 | 100.00 |
| | | W/Co | | 0.82 | 0.26 |

Example 4

| Atomic # | Symbol | Name | Atomic Wt | Weight % | Atomic % |
|---|---|---|---|---|---|
| 1 | H | Hydrogen | 1.00794 | 0.00 | 0.00 |
| 5 | B | Boron | 10.811 | 0.00 | 0.00 |
| 6 | C | Carbon | 12.0107 | 0.00 | 0.00 |
| 7 | N | Nitrogen | 14.0067 | 0.00 | 0.00 |
| 8 | O | Oxygen | 15.9994 | 0.00 | 0.00 |
| 14 | Si | Silicon | 28.0855 | 0.20 | 0.47 |
| 15 | P | Phosphorous | 30.97376 | 0.02 | 0.04 |
| 16 | Si | Sulfur | 32.065 | 0.02 | 0.03 |
| 24 | Cr | Chromium | 51.9961 | 20.00 | 25.31 |
| 25 | Mn | Manganese | 54.93805 | 1.50 | 1.80 |
| 26 | Fe | Iron | 55.845 | 1.50 | 1.77 |
| 27 | Co | Cobalt | 58.9332 | 31.76 | 40.02 |
| 28 | Ni | Nickel | 58.6934 | 10.00 | 11.21 |
| 74 | W | Tungsten | 183.84 | 35.00 | 14.14 |
| 77 | Ir | Iridium | 192.217 | 0.00 | 0.00 |
| 78 | Pt | Platinum | 195.084 | 0.00 | 0.00 |
| 103 | Lr | Lawrencium | 262 | 0.00 | 0.00 |
| | | Total | | 100.00 | 100.00 |
| | | W/Co | | 1.10 | 0.35 |

As shown above, in an example, the alloy may consist essentially of Co, Cr, Ni, and W, where any additional elements that may be present, may be present at less than 2% by weight (e.g., particularly in the case of Mn and/or Fe), less than 1%, or less than 0.5%, or less than 0.25% (e.g., particularly in the case of Si, P, and/or S), if at all.

Figure 7:
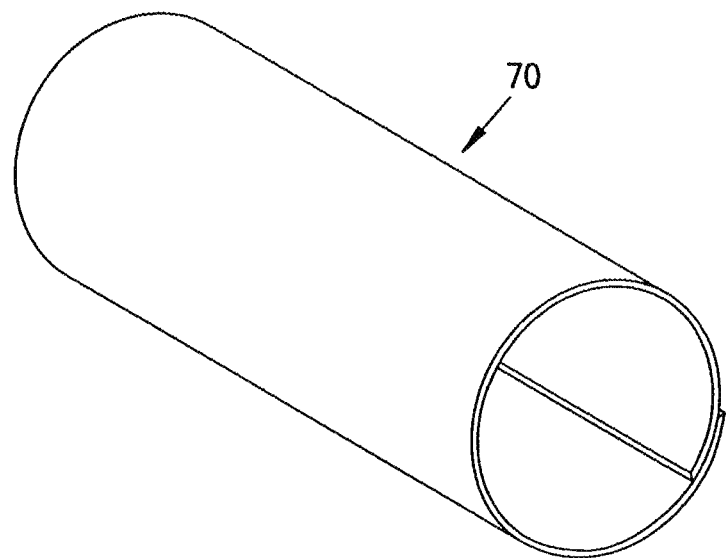
FIG. 7 is a perspective view of a tubular embodiment of a radiopaque stent of that can be formed according to the present invention.
Figures 8A, 8B:
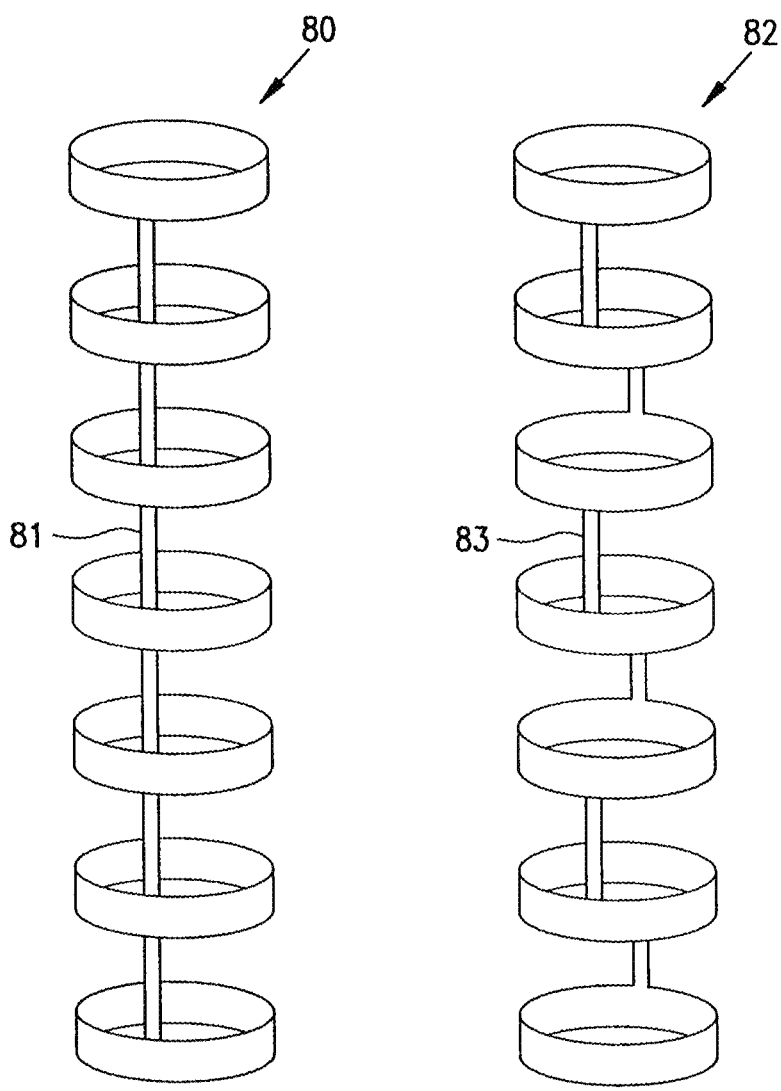
FIG. 8a is a perspective view of a configuration of a radiopaque stent that includes a backbone that can be formed according to the present invention.
FIG. 8b is a perspective view of another configuration of a radiopaque stent that includes a staggered backbone that can be formed according to the present invention.
Figure 9:
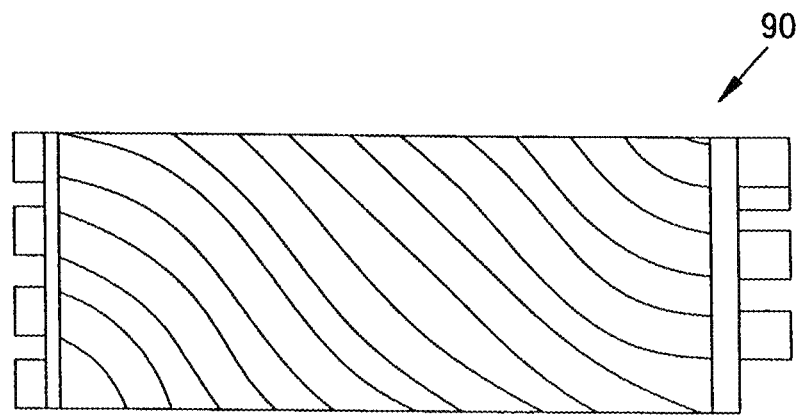
FIG. 9 is a side view of a coiled configuration of a radiopaque stent that can be formed according to the present invention.
Figure 10:
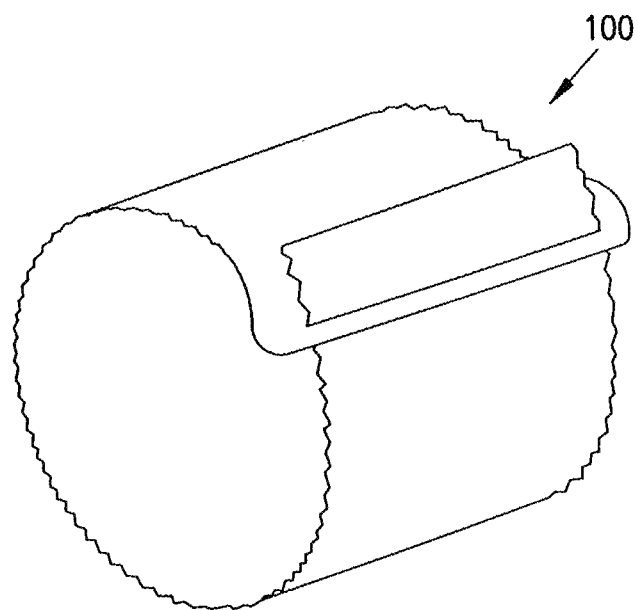
FIG. 10 is a perspective view of a ratcheted configuration of a radiopaque stent that can be formed according to the present invention.

The radiopaque stent of the present invention may be fabricated according to any number of configurations. Non-limiting exemplary configurations include a solid cylinder, illustrated at 70 in FIG. 7, a coiled stent illustrated at 90 in FIG. 9, a ratcheting stent 100, illustrated in FIG. 10, a stent embodiment 80 with a backbone 81, illustrated in FIG. 8a or a stent embodiment 82 with a staggered backbone 83, illustrated in FIG. 8b. Additional configurations are shown in FIGS. 4-5a. In an embodiment, the entirety of the stent body may be formed from the radiopaque Co—Cr alloy described herein (e.g., without various metallic layers, markers, or the like).

One type of radiopaque stent design embodiment is a high precision patterned cylindrical device. An example of such is illustrated generally at 10 in FIG. 1. The stent 10 typically comprises a plurality of radially expanded cylindrical elements 12 disposed generally coaxially and interconnected by elements 13 disposed between adjacent cylindrical elements.

Figure 2:
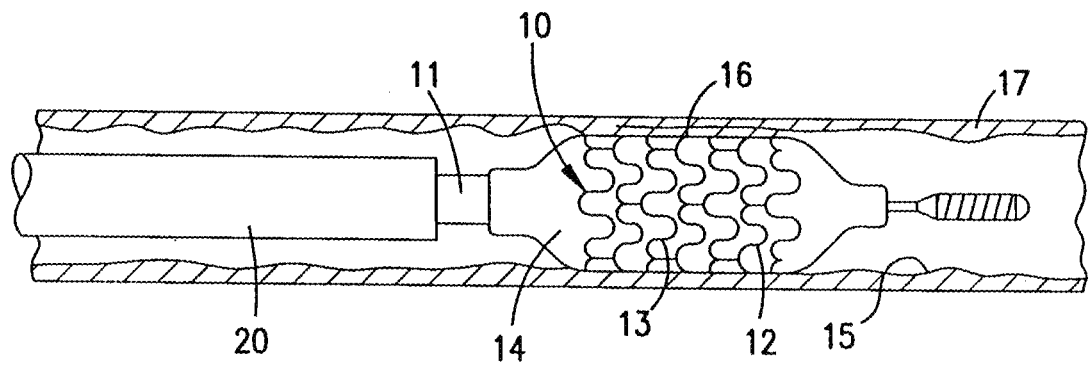
FIG. 2 is an elevational view, partially in section, showing the radiopaque stent of FIG. 1 within a damaged lumen.

For some embodiments, the stent 10 is expanded by a delivery catheter 11. The delivery catheter 11 has an expandable portion or a balloon 14 for expanding of the stent 10 within an artery 15. Prior to expansion, the delivery catheter 11 and balloon 14 may be encased in a stent covering 20. FIG. 1 illustrates an example of the delivery catheter 11 and balloon 14 within the stent covering 20 while FIG. 2 illustrates an example of the delivery catheter 11 and balloon 14 expanded beyond the stent covering 20. The delivery catheter 11 onto which the stent 10 is mounted is similar to a conventional balloon dilation catheter used for angioplasty procedures. The artery 15, as shown in FIG. 1, has a lining 17 and a dissected lining 16 which has occluded a portion of the arterial passageway.

Each radially expandable cylindrical element 12 of the radiopaque stent 10 is independently expandable. Therefore, the balloon 14 may be provided with an inflated shape other than cylindrical, e.g., tapered, to facilitate implantation of the stent 10 in a variety of body lumen shapes.

The delivery of the radiopaque stent 10 is accomplished by mounting the stent 10 onto the inflatable balloon 14 on the distal extremity of the delivery catheter 11. The catheter-stent assembly is introduced within the patient's vasculature using conventional techniques through a guiding catheter which is not shown. A guidewire 18 is disposed across the damaged arterial section and then the catheter-stent assembly is advanced over a guidewire 18 within the artery 15 until the stent 10 is directly under detached lining 16 of the damaged arterial section. The balloon 14 of the catheter is expanded, expanding the stent 10 against the artery 15, which is illustrated in FIG. 2. While not shown in the drawing, the artery 15 is preferably expanded slightly by the expansion of the stent 10 to seat or otherwise fix the stent 10 to prevent movement. In some circumstances during the treatment of a stenotic portion of an artery, the artery may have to be expanded considerably in order to facilitate passage of blood or other fluid therethrough. This expansion is easily observable by the interventionalist with the radiopaque stent of the present invention. While balloon expandable stents are described, it will be appreciated that the alloys and configurations described herein may, in at least some embodiments, be self-expanding.

Figure 3:
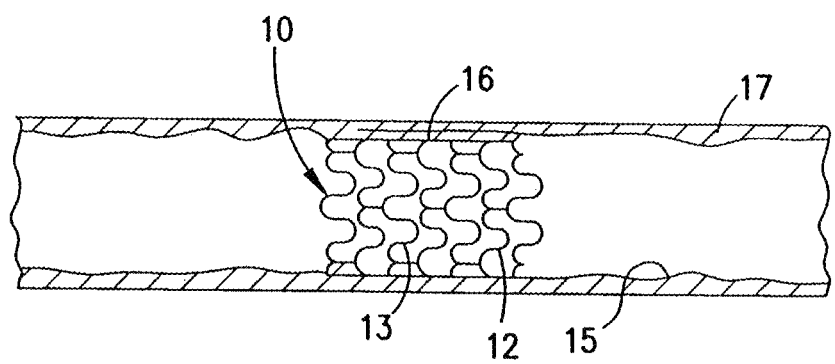
FIG. 3 is an elevational view, partially in section, showing the radiopaque stent of FIG. 1 expanded within the lumen after withdrawal of the delivery catheter.

The stent 10 serves to hold open the artery 15 after the catheter 11 is withdrawn, as illustrated in FIG. 3. Due to the formation of the stent 10 from the elongated tubular member, the undulating component of the cylindrical elements of the stent 10 is relatively flat in transverse cross section so that when the stent is expanded, the cylindrical elements are pressed into the wall of the artery 15 and as a result do not interfere with the blood flow through the artery 15. The cylindrical elements 12 of the stent 10 which are pressed into the wall of the artery 15 are eventually covered with endothelial cell growth which further minimizes blood flow interference. The undulating pattern of the cylindrical sections 12 provides good characteristics to prevent stent movement within the artery. Furthermore, the closely spaced cylindrical elements at regular intervals provide uniform support for the wall of the artery 15, and consequently are well adapted to tack up and hold in place small flaps or dissections in the wall of the artery 15 as illustrated in FIGS. 2 and 3. The undulating pattern of the radiopaque stent is readily discernable to the interventionalist performing the procedure.

FIG. 4 is an enlarged perspective view of the stent 10 shown in FIG. 1 with one end of the stent shown in an exploded view to illustrate in greater detail the placement of interconnected elements 13 between adjacent radially expandable cylindrical elements 12. Each pair of interconnecting elements 13 on one side of the cylindrical element 12 are positioned to achieve maximum flexibility for the stent 10. In an embodiment shown in FIG. 4, the stent 10 has three interconnecting elements 13 between adjacent radially expandable cylindrical elements 12 which are 120 degrees apart. Each pair of interconnecting elements 13 on one side of a cylindrical element 12 are offset radially 60 degrees from the pair on the other side of the cylindrical element. The alternation of the interconnecting elements results in a stent which is longitudinally flexible in essentially all directions. Various configurations for the placement of interconnecting elements are possible. However, as previously mentioned, all of the interconnecting elements of an individual stent are secured to either the peaks or valleys of the undulating structural elements in order to prevent shortening of the stent during the expansion thereof.

The number of undulations may be varied to accommodate placement of interconnecting elements 13, e.g., at the peaks of the undulations or along the sides of the undulations as shown in FIG. 5.

As best observed in FIGS. 4 and 5, cylindrical elements 12 are in the form of a serpentine pattern 30. FIG. 5A illustrates an example cross-section view 35 along the line 5a-5a of FIG. 5. FIG. 5A illustrates the cylindrical element 12 with two edges 34. As previously mentioned, each cylindrical element 12 is connected by interconnecting elements 13. Serpentine pattern 30 is made up of a plurality of U-shaped members 31, W-shaped members 32 and Y-shaped members 33, each having a different radius so that expansion forces are more evenly distributed over the various embodiments.

The illustrative stent 10 and other stent structures can be made using several techniques, including laser machining. One method of making the radiopaque stent is to cut a thin walled tubular member made of the radiopaque Co—Cr—Ni—W alloy described herein, to remove portions of the tubing in a desired pattern for the stent, leaving relatively untouched the portions of the radiopaque Co—Cr—Ni—W alloy tubing which are to form the stent. In accordance with one method of making the device of the present invention, the tubing is cut in a desired pattern using a machine-controlled laser as illustrated schematically in FIG. 6.

Typically, before crimping, the stent has an outer diameter on the order of about 0.04 to 0.10 inches in the unexpanded condition, approximately the same outer diameter of the tubing from which it is made, and may be expanded to an outer diameter in a range of about 1 to 15 millimeters. Stents for peripheral and other larger vessels may be constructed from larger diameter tubing. The strut thickness in a radial direction is in a range of 0.001 to 0.01 inches.

Figure 6:
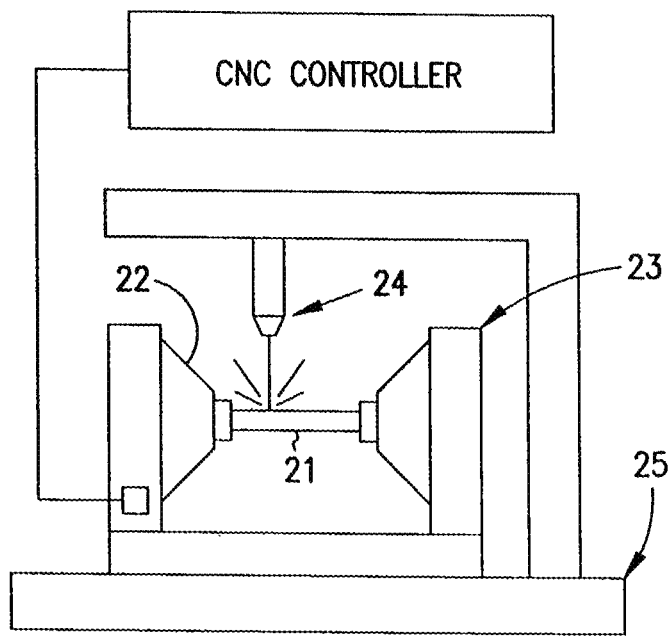
FIG. 6 is a schematic representation of equipment for selectively cutting the tubing in the manufacture of the radiopaque stent of the present invention.

Referring to FIG. 6, in one fabrication embodiment, the tubing 21 is put in a rotatable collet fixture 22, of a machine controlled apparatus 23 for positioning the tubing 21 relative to a laser 24. According to machine-encoded instructions, the tubing 21 is rotated and moved longitudinally relative to the laser 24 which is also machine controlled. The laser selectively removes the material from the tubing by ablation and a pattern is cut into the tube. The tube is therefore cut into the discrete pattern of the finished stent.

The process for cutting a pattern for the stent into the tubing may be automated except for loading and unloading the length of tubing. Referring again to FIG. 6, it may be done, for example, using a CNC opposing collet fixture 22 for axial rotation of the length of tubing. In conjunction with a CNC X-Y table 25 to move the length of tubing axially relatively to a machine-controlled laser as described. The entire space between collets is patterned using a laser setup of the foregoing example. The program for control of the apparatus is dependent on the particular configuration used.

The tubes are made of a Co—Cr—Ni—W alloy as described herein that include super-saturated tungsten content (e.g., 20-35% tungsten by weight), while maintaining primarily single-phase characteristics within the alloy. The tubes have an outside diameter of 0.04 inches to 0.10 inches and a wall thickness of 0.001 inches to 0.010 inches. In one embodiment, the tubes are fixed under a laser and are positioned using a CNC to generate a very intricate and precise pattern. Due to the thin wall and the small geometry of the stent pattern, it is necessary to have very precise control of the laser, its power level, the focus spot size and the precise positioning of the laser cutting path.

One reason to have precise control of the laser operating parameters is to minimize heat input into the stent structure, which prevents thermal distortion, uncontrolled burnout of the metal, and metallurgical damage from excessive heat. It can also be important to minimize or otherwise control heating of the stent structure which might undesirably alter the desired single-phase structure, particularly given the super-saturated tungsten content present in the alloy. With such lasers, it is possible to make a smooth, narrow cut in the Co—Cr—Ni—W alloy tubes in very fine geometries without damaging the narrow struts that make up the stent structure, and without undesirably altering the phase characteristics. The system of the present invention using such lasers and their available parameter adjustments, makes it possible to cut using a narrow beam which minimizes the heat input into the material.

The positioning of the cylindrical radiopaque Co—Cr—Ni—W alloy structure benefits from use of precision CNC equipment. In addition, for some embodiments, a rotary mechanism can be provided that allows the computer program to be written as if the pattern were being cut from a flat sheet. This allows both circular and linear interpolation to be used in programming.

The optical system which expands the original laser beam delivers the beam through a viewing head and focuses the beam onto the surface of the tube, may include a coaxial gas jet and nozzle that helps remove debris from the cut face and cools the region where the beam interacts with the material as the beam cuts and vaporizes the metal. Such is also advantageous to block the beam as it cuts the top surface of the tube and prevent the beam, along with the molten metal and debris from the cut, from impinging on the opposite surface of the tube.

In addition to the laser and the CNC positioning equipment, the optical delivery system can include a beam expander to increase the laser beam diameter, a circular polarizer, typically in the form of a quarter wave plate, to eliminate polarization effects in metal cutting, provisions for a spatial filter, a binocular viewing head and focusing lens, and a coaxial gas jet that provides for the introduction of a gas stream which surrounds the focus beam and is directed along the beam axes.

The cutting process typically uses an assist gas with the laser beam, resulting in a narrow cut area and minimal molten slag along the cut. In order to remove the slag debris from the cut allowing the scrap to be removed from the remaining stent pattern, the cut tube can be soaked in an appropriate solution of mineral acids. Before it is soaked, the tube may be ultrasonically cleaned in a mineral acid solution after cutting.

Direct laser cutting produces edges which are essentially perpendicular to the axes of the laser cutting beam in contrast with chemical etching and the like which may produce patterned edges which are angled. Hence, the laser cutting process essentially provides stent cross sections from cut-to-cut which are square or rectangular. As depicted, cylindrical elements 12 are comprised of struts 30 which have generally rectangular cross sections 32 wherein the stent is laser cut from a tubular member. The struts have generally perpendicular edges 31 formed by the laser cut. The resulting stent structure provides superior performance. That said, it is possible to form stents according to the present invention using techniques other than laser cutting, while still providing benefits associated with the enhanced radiopacity, primarily single-phase alloy with super-saturated tungsten content, without resorting to expensive exotic metal elements, as described herein.

In other embodiments, the radiopaque Co—Cr—Ni—W alloy stent of the present invention is fabricated of radiopaque Co—Cr—Ni—W alloy wire elements. In another embodiment, the stent is made of a radiopaque Co—Cr—Ni—W alloy flat stock. In another embodiment, the stent is made of radiopaque Co—Cr—Ni—W alloy materials using near-net shape processing such as metal injection molding.

When expanded, the stent may cover about 10-45% of an arterial wall surface area. The radiopaque Co—Cr—Ni—W alloy stent of the present invention can withstand at least about 30% tensile deformation before failure.

Although described principally for use in manufacturing stents, it will be understood that any of the disclosed alloys may also be used in the manufacture of guide wires, guide wire tip coils, balloon markers, or other structures associated with catheter use, and other implantable structures in which improved radiopacity would be desirable.

The present invention can be embodied in other specific forms without departing from its spirit or essential characteristics. Thus, the described implementations are to be considered in all respects only as illustrative and not restrictive. The scope of the invention is, therefore, indicated by the appended claims rather than by the foregoing description. All changes that come within the meaning and range of equivalency of the claims are to be embraced within their scope.

The invention claimed is:

1. A process for the production of a primarily single-phase FCC, cobalt-chromium alloy including tungsten, the process comprising:
   forming an alloy melt including cobalt, chromium, nickel and tungsten, the tungsten being at least 20% to about 35% by weight of a solution, so that the tungsten content is above a solubility limit of tungsten in the cobalt-chromium alloy at ambient temperature and the chromium is 15% to 25% by weight of the solution;
   heating the alloy melt to at least about 1500° C. for a time sufficient to form a single-phase solution;
   cooling, without water quenching, the single-phase solution to 500K within a period of time of less than 10 minutes to preserve a primarily single-phase FCC solid solution structure, wherein no more than 10% volume fraction of a second phase is present, the second phase having an average particle size of less than 15 μm, even with the super-saturated tungsten content.

2. The process of claim 1, wherein the solution comprises nickel in an amount from about 5% to about 15% by weight of the solution.

3. The process of claim 1, wherein the cooling step is performed within a period of time of less than 1 minute.

4. The process of claim 1, wherein the cooling step is performed by spraying the single-phase solution through a nozzle in order to form droplets of the single-phase solution.

5. The process of claim 4, further comprising
cooling the droplets of the single phase solution into a powder,
compacting the powder, and
sintering the compacted powder into a billet.

6. The process of claim 1, wherein the cooling step includes pouring the single-phase solution onto a spinning drum in order to form a ribbon, wherein the spinning drum is cooled.

7. The process of claim 1, wherein the process for producing a primarily single-phase FCC, cobalt-chromium alloy including super saturated tungsten content comprises a physical vapor deposition process.

8. The process of claim 1, wherein the solution comprises cobalt in an amount from about 30% to about 50% by weight of the solution.

9. The process of claim 1, wherein the solution comprises nickel in an amount of about 10% by weight of the solution.

10. The process of claim 1, wherein the solution is entirely free of molybdenum.

11. The process of claim 1, wherein the cobalt-chromium alloy is substantially free of carbon.

12. The process of claim 1, wherein the solution is entirely free of carbon.

13. The process of claim 1, wherein the solution comprises no more than 1% of each of silicon, phosphorus, and sulfur by weight.

14. The process of claim 1, wherein the solution further comprises manganese in a concentration up to 5% by weight of the solution.

15. The process of claim 1, wherein the solution further comprises iron in a concentration up to 5% by weight of the solution.

16. The process of claim 1, wherein the cobalt-chromium alloy further comprises both manganese and iron in a concentration of about 1.5% each, by weight.

17. The process of claim 1, wherein a sum of cobalt and tungsten comprises from about 66 to 68% by weight of the cobalt-chromium alloy.

18. The process of claim 1, wherein the solution is maintained at at least about 1500° C. for 1 minute to 30 minutes to ensure that the solution has sufficient time to reach an equilibrium state in which the single-phase FCC structure is attained.

19. The process of claim 1, wherein a weight percent ratio of tungsten to cobalt is from 0.4 to 1.2.

20. A process for the production of a stent from a primarily single-phase FCC, cobalt-chromium alloy including tungsten, the process comprising:
forming a solution including cobalt, chromium, nickel and tungsten, the solution being entirely free of carbon and molybdenum and not including any other alloying elements in amounts greater than 3% by weight;
the tungsten being 25% to 30% by weight of the solution, so that the tungsten content is above a solubility limit of tungsten in the cobalt-chromium alloy at ambient temperature;
the nickel comprising about 10% by weight of the solution;
the chromium is 15% to 25% by weight of the solution;
heating the solution to a temperature of at least about 1300° C., and maintaining the solution at said temperature for a time period of at least 1 minute to ensure that the solution has sufficient time to reach an equilibrium state in which the single-phase FCC structure is attained; and
cooling the single-phase solution from at least 1300° C. to 500K at a rate of about 200° C./second to about 500° C./second within a period of time of less than 5 minutes to preserve a primarily single-phase FCC solid solution structure, even with the super-saturated tungsten content.

21. A process for the production of a single-phase FCC, cobalt-chromium alloy including tungsten, the process comprising:
forming a solid solution including cobalt, chromium, nickel and tungsten, the tungsten being 25% to about 35% by weight of the solid solution, so that the tungsten content is above a solubility limit of tungsten in the cobalt-chromium alloy at ambient temperature, the chromium is 15% to 25% by weight of the solution, wherein the solid solution is entirely free of carbon and molybdenum;
heating the solid solution to at least about 1300° C. for a time sufficient to form a single-phase solution;
cooling, without water quenching, the single-phase solution to 500K at a rate of about 200° C./second to about 500° C./second within a period of time of less than 10 minutes to preserve a single-phase FCC solid solution structure in a resultant alloy material, even with the super-saturated tungsten content;
heating the alloy material to at least 600° C. for at least 1 hour to form fine particulate $Co_3W$ while preserving the primarily single-phase FCC solid solution structure in the alloy material.

* * * * *